US011572572B2

(12) United States Patent
Chen et al.

(10) Patent No.: US 11,572,572 B2
(45) Date of Patent: Feb. 7, 2023

(54) A138T MUTATION-CONTAINING PLANT EPSPS MUTANT, AND ENCODING GENE AND APPLICATION THEREOF

(71) Applicant: GEVOTO LLC, Sichuan (CN)

(72) Inventors: Rong Chen, Sichuan (CN); Longqun Deng, Sichuan (CN); Qingjiang Hou, Sichuan (CN); Yuangen Lu, Sichuan (CN); Qian Ou, Sichuan (CN); Xiaorong Feng, Sichuan (CN); Ling Li, Sichuan (CN); Xin Huang, Sichuan (CN); Nanfei Xu, Sichuan (CN)

(73) Assignee: GEVOTO LLC, Sichuan (CN)

( * ) Notice: Subject to any disclaimer, the term of this patent is extended or adjusted under 35 U.S.C. 154(b) by 218 days.

(21) Appl. No.: 16/761,123

(22) PCT Filed: Dec. 14, 2018

(86) PCT No.: PCT/CN2018/121330
§ 371 (c)(1),
(2) Date: May 1, 2020

(87) PCT Pub. No.: WO2019/086050
PCT Pub. Date: May 9, 2019

(65) Prior Publication Data
US 2020/0377868 A1 Dec. 3, 2020

(30) Foreign Application Priority Data

Nov. 2, 2017 (CN) .......................... 201711062151.X
Sep. 13, 2018 (CN) .......................... 201811070642.3

(51) Int. Cl.
*C12N 15/82* (2006.01)
*C12N 9/10* (2006.01)

(52) U.S. Cl.
CPC ....... *C12N 15/8275* (2013.01); *C12N 9/1092* (2013.01); *C12Y 205/01019* (2013.01)

(58) Field of Classification Search
CPC ................................................ C12N 15/8275
See application file for complete search history.

(56) References Cited

FOREIGN PATENT DOCUMENTS

| CN | 1196088 A | 10/1998 |
|---|---|---|
| CN | 1358858 A | 7/2002 |
| CN | 102559708 A | 7/2012 |
| CN | 104630245 A | 5/2015 |
| CN | 105586353 A | 5/2016 |
| CN | 106636025 A | 5/2017 |
| CN | 107267480 A | 10/2017 |
| CN | 105969782 A | 9/2019 |

OTHER PUBLICATIONS

Padgette et al, J. of Biol. Chem. (1991) 266:22364-22369.*
First Office Action issued in Application No. 201811070642-3 dated May 22, 2019.
Second Office Action issued in Application No. 201811070642-3 dated May 22, 2019, with English-language translation.
International Search Report issued in PCT/CN2018/121330 dated Mar. 13, 2019, with English-language translation.
Written Opinion issued in PCT/CN2018/121330 dated Mar. 13, 2019.
Chen et al., Mutations and amplification of EPSPS gene confer resistance to glyphosate in goosegrass (*Eleusine indica*), Planta. (2015) 242:859-868.
Zhang et al., Characterization and Site-Directed mutagenesis of a novel class II 5-enopyruvylshikamate-3-phosphate (EPSP) synthase from the deep sea bacterium Alcanivoraz sp.L27, Enzyme and Microbial Technology, 63 (2014) pp. 64-70.
Healy-Fried et al., "Structural Basis of Glyphosate Tolerance Resulting from Mutations of Pro101 in *Escherichia coli* 5-enolpyruvylshikimate-3-phosphate synthase," The Journal of Biological Chemistry, vol. 262, No. 45, pp. 32949-32955, Nov. 9, 2007.
First Office Action from related application CA 3,081,376, dated May 21, 2021.
English Translation of the Written Opinion issued in PCT Application No. PCT/CN2018/121330, dated Mar. 13, 2019.

* cited by examiner

*Primary Examiner* — Mykola V. Kovalenko
(74) *Attorney, Agent, or Firm* — Hogan Lovells US LLP

(57) ABSTRACT

The invention provides a plant EPSPS mutant (i.e., 5-enolpyruvylshikimate-3-phosphate synthase mutant), which is derived from a plant and is mutated to have glyphosate resistance. Also provided is an encoding gene, which can encode the plant EPSPS mutant. In addition, a vector containing the encoding gene and a cell containing the vector is provided by the invention. Further, a use of the plant EPSPS mutant is provided.

12 Claims, 4 Drawing Sheets

Specification includes a Sequence Listing.

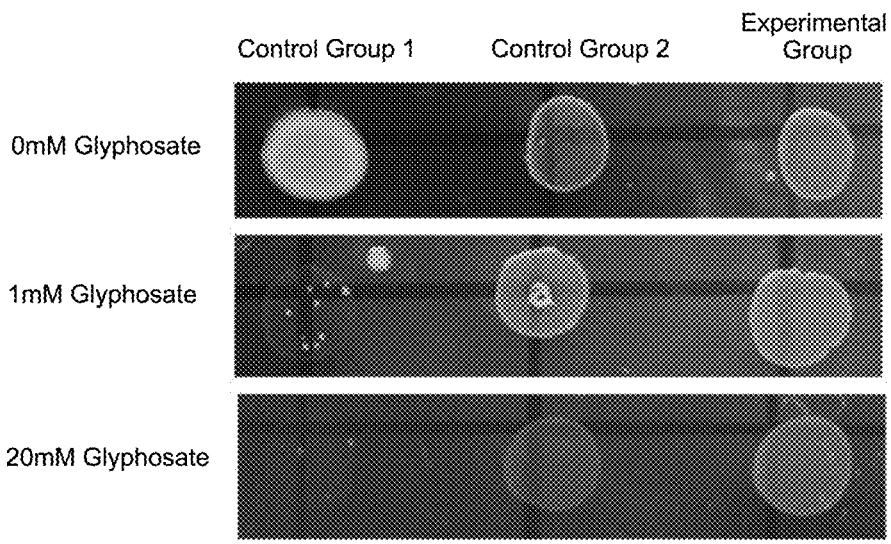

FIG. 3

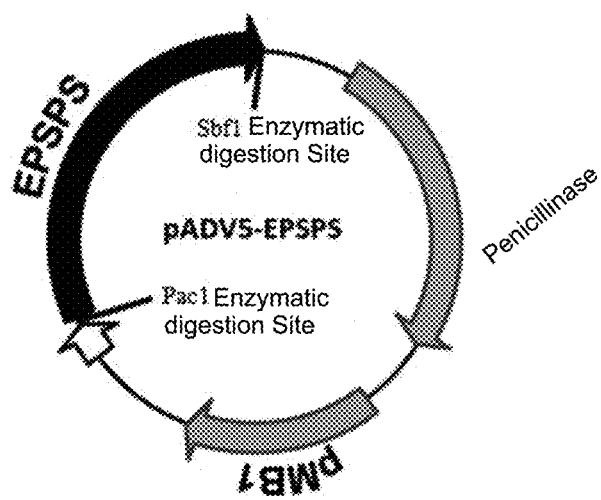

FIG. 4

```
                                                              ↓
Ec-EPSPS WT  NALTALGVSYTLSADRTRCEIIGNGGPLH----AEGALELFLGNAGTAMRPLAAA  105
Os-EPSPS M   EALKALGLSVEADKVAKRAVVVGCGGKFPVEKDAKEEVQLFLGNAATAMRPLTAA  120
Os-EPSPS WT  EALKALGLSVEADKVAKRAVVVGCGGKFPVEKDAKEEVQLFLGNAGTAMRPLTAA  120
                                                              ↓
Ec-EPSPS WT  LAAALCL--GSNDIVLTGEPRMKERPIGHLVDALRLGGAKITYLEQENYPPLRLQ  154
Os-EPSPS M   LTAAVTAAGGNATYVLDGVPRMRERPIGDLVVGLKQLGTDVDCFLGTECPPVRVK  171
Os-EPSPS WT  LTAAVTAAGGNATYVLDGVPRMRERPIGDLVVGLKQLGADVDCFLGTECPPVRVK  171
```

FIG. 5

```
Ec-EPSPS WT  LNALTALGVSYTLSADRTRCEIIGNGGPLH---AEGALELFLGNAGTAMRPLAAA 105
Z-EPSPS M    LGALRTLGLSVEADKAAKRAVVVGCGGKFPVEDSIEEVQLFLGNAATAMRSLTAA 114
Z-EPSPS WT   LGALRTLGLSVEADKAAKRAVVVGCGGKFPVEDSKEEVQLFLGNAGTAMRPLTAA 114

Ec-EPSPS WT  LAAALCL-GSNDIVLTGEPRMKERPIGHLVDALRLGGAKITYLEQENYPPLRLQ 154
Z-EPSPS M    LTAAVTAAGGNATYVLDGVPRMRERPIGDLVVGLKQLGTDVDCFLGTDCPPVRVN 165
Z-EPSPS WT   LTAAVTAAGGNATYVLDGVPRMRERPIGDLVVGLKQLGADVDCFLGTDCPPVRVN 165
```

FIG. 6

```
Ec-EPSPS WT  NALTALGVSYTLSADRTRCEIIGNGGPLH-----AEGALELFLGNAGTAMRPLAAA 105
T-EPSPS M    EALEALGLSVEADKVAKRAVVVGCGGRFPVEKDAKEEVKLFLGNAATAMRSLTAA 122
T-EPSPS WT   EALEALGLSVEADKVAKRAVVVGCGGRFPVEKDAKEEVKLFLGNAGTAMRPLTAA 122

Ec-EPSPS WT  LAAALCL-GSNDIVLTGEPRMKERPIGHLVDALRLGGAKITYLEQENYPPLRLQ 154
T-EPSPS M    LTAAVVAAGGNATYVLDGVPRMRERPIGDLVVGLQQLGTDVDCFLGTNCPPVRIN 173
T-EPSPS WT   LTAAVVAAGGNATYVLDGVPRMRERPIGDLVVGLQQLGADVDCFLGTNCPPVRIN 173
```

FIG. 7

A138T MUTATION-CONTAINING PLANT EPSPS MUTANT, AND ENCODING GENE AND APPLICATION THEREOF

CROSS-REFERENCE TO RELATED APPLICATIONS

This application is a national stage application of PCT/CN2018/121330 filed on Dec. 14, 2018, the disclosure of which is incorporated herein by reference in entirety. The present disclosure claims priority to Chinese Patent Application No. 201711062151.X, filed with the Chinese Patent Office on Nov. 2, 2017, entitled "A138T Mutation-Containing Plant EPSPS Mutant, and Encoding Gene and Application Thereof", and Chinese Patent Application No. 201811070642.3, filed with the Chinese Patent Office on Sep. 13, 2018, entitled "A138T Mutation-Containing Plant EPSPS Mutant, and Encoding Gene and Application Thereof", which are incorporated herein by reference in their entireties.

TECHNICAL FIELD

The present disclosure relates to the technical field of genetic engineering, and in particular to a plant EPSPS mutant containing an A138T mutation, a gene encoding the same, and use thereof.

BACKGROUND ART

Glyphosate is one of the herbicides currently most widely used in the world, which has been used for nearly 40 years. Glyphosate inhibits the activity of 5-enolpyruvylshikimate-3-phosphate synthase (EPSPS). EPSPS catalyzes the synthesis of EPSP from PEP and shikimate-3-phosphate in the shikimate pathway, and finally aromatic amino acids, e.g., tryptophan, phenylalanine, and tyrosine are synthesized. Glyphosate blocks the synthesis of the aromatic amino acids, which in turn affects the normal growth of a plant and eventually leads to death of the plant.

In the current methods of cultivating (or breeding) glyphosate-resistant varieties, glyphosate-resistant genes from bacteria are introduced into crops by using genetic engineering means so as to cultivate new varieties of transgenic (or genetically modified) glyphosate-resistant crops. Since widespread planting in 1996, the glyphosate-resistant transgenic crops have been planted over a rapidly increasing area. By 2015, the glyphosate-resistant transgenic crops have been planted over an area of 150 million hectares in the world, which accounts for 83% of the total area of the planted transgenic crops and by which huge benefits have been brought to the agriculture production and environment.

However, the glyphosate-resistant gene currently most widely used in agriculture is CP4 EPSPS derived from *Agrobacterium tumefaciens* strain CP4. Although many EPSPS genes resistant to glyphosate have been successively found from microorganisms, these genes have not been widely used in crops. Use of these glyphosate-resistant genes from microorganisms in crops involves expression of these genes such as CP4 EPSPS in the crops by a transgenic method. Although the resulting transgenic crops have been planted widespread over a quite large area, public acceptance of transgenic crops is still a major issue around the globe. Even in the Americas with the largest area of planted transgenic crops, the transgenic crops are limited mainly to several crops such as corn, soybean, and cotton.

SUMMARY

An object of the present disclosure is to provide a plant EPSPS mutant (i.e., 5-enolpyruvylshikimate-3-phosphate synthase mutant), which is derived from a plant and is mutated to have glyphosate resistance.

A further object of the present disclosure is to provide an encoding gene, which can encode the plant EPSPS mutant described above.

A further object of the present disclosure is to provide a vector containing the encoding gene described above.

A further object of the present disclosure is to provide a cell containing the vector described above.

A further object of the present disclosure is to provide use of the plant EPSPS mutant described above.

The present disclosure is implemented as follows:

a plant EPSPS mutant, the plant EPSPS mutant comprising an amino acid sequence having a mutation A>T at a site corresponding to position 138 of an amino acid sequence of *Escherichia coli* EPSPS, compared to *Escherichia coli* EPSPS;

an encoding gene encoding the plant EPSPS mutant described above;

a vector containing the encoding gene described above;

a recombinant cell containing the vector described above;

use of the plant EPSPS mutant described above in the cultivation of a glyphosate-resistant plant.

The Present Disclosure has the Following Advantageous Effects

The present disclosure provides a plant EPSPS mutant, the plant EPSPS mutant comprising an amino acid sequence having a mutation A>T at a site corresponding to position 138 of an amino acid sequence of *Escherichia coli* EPSPS, compared to *Escherichia coli* EPSPS. This mutation site corresponds to amino acid residues at position 155 of *Oryza sativa* EPSPS, position 149 of *Zea mays* EPSPS, and position 157 of *Triticum aestivum* EPSPS, at which a mutation from A to T occurs. The mutation significantly increases the glyphosate resistance of different mutants of EPSPS of various plants while maintaining their own biological enzymatic catalytic activity. All of plants or recombinant bacteria transformed with the plant EPSPS mutants according to the present disclosure can grow normally in the presence of glyphosate. The plant EPSPS mutants can be used not only for the cultivation of transgenic crops, but also for the cultivation of glyphosate-resistant non-transgenic plants such as rice, tobacco, soybean, corn, wheat, cotton, sorghum, and the like, and thus have wide application prospects.

SEQUENCE LISTING

This application includes a sequence listing, which is herein incorporated by reference and was filed electronically as an ASCII text file and entitled "046231-000042-replacementSL.txt" and it was created on Jun. 2, 2020 and is 75 kb.

BRIEF DESCRIPTION OF DRAWINGS

In order to more clearly illustrate technical solutions of embodiments of the present disclosure, drawings required for use in the embodiments will be described briefly below. It is to be understood that the drawings below are merely illustrative of some embodiments of the present disclosure, and therefore should not be considered as limiting its scope.

It will be understood by those of ordinary skill in the art that other relevant drawings can also be obtained from these drawings without any inventive effort.

FIG. 3 is a view showing results of growth of an *Escherichia coli* strain transformed with a gene encoding a *Triticum aestivum* EPSPS mutant according to Example 3 in media containing different concentrations of glyphosate in Example 7 of the present disclosure;

FIG. 4 is a schematic structural view of a pADV5 vector in Example 5 of the present disclosure;

FIG. 5 shows a partial result of alignment of amino acid sequences of *Escherichia coli* EPSPS, *Oryza sativa* EPSPS mutant II, and wild-type *Oryza sativa* EPSPS in Example 2 of the present disclosure;

FIG. 6 shows a partial result of alignment of amino acid sequences of *Escherichia coli* EPSPS, the *Zea mays* EPSPS mutant, and wild-type *Zea mays* EPSPS in Example 3 of the present disclosure;

FIG. 7 shows a partial result of alignment of amino acid sequences of *Escherichia coli* EPSPS, the *Triticum aestivum* EPSPS mutant, and wild-type *Triticum aestivum* EPSPS in Example 4 of the present disclosure.

DETAILED DESCRIPTION OF EMBODIMENTS

Figure 1:
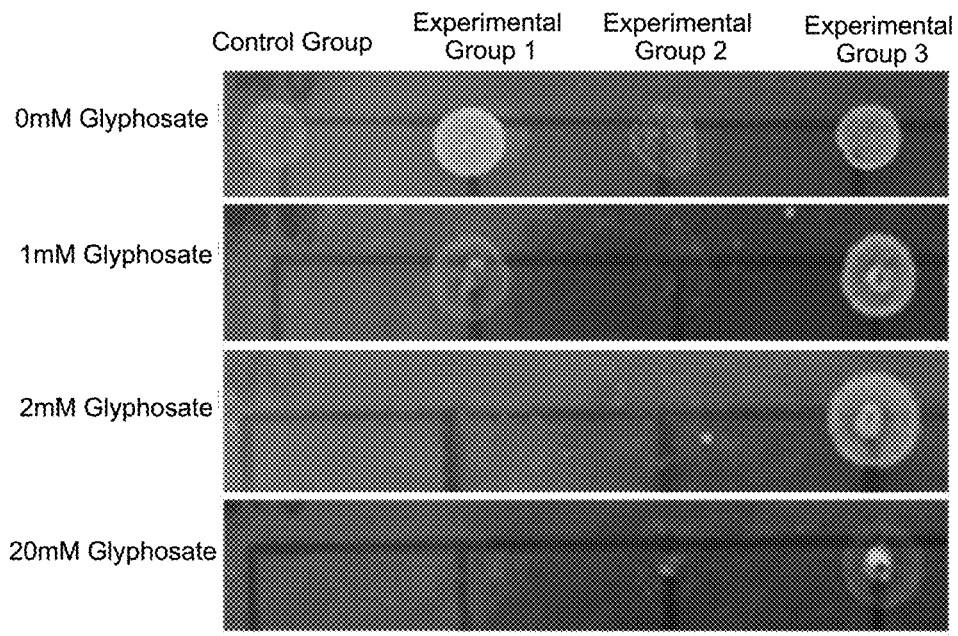
FIG. 1 is a view showing results of growth of an *Escherichia coli* (*E. coli*) strain transformed with a gene encoding an *Oryza sativa* EPSPS mutant according to Example 1 in media containing different concentrations of glyphosate in Example 5 of the present disclosure.

In order to further clarify the objects, technical solutions, and advantages of the examples of the present disclosure, the technical solutions of the examples of the present disclosure will be described below clearly and completely. Examples are carried out in accordance with conventional conditions or conditions recommended by manufacturers if no specific conditions are specified in the examples. Reagents or instruments used, whose manufacturers are not specified, are all conventional products that are available commercially.

A plant EPSPS mutant containing an A138T mutation, a gene encoding the same, and use thereof according to the present disclosure will be described in detail below.

In one aspect, the present disclosure provides a plant EPSPS mutant (i.e., a mutant of 5-enolpyruvylshikimate-3-phosphate synthase), the plant EPSPS mutant comprising an amino acid sequence having a mutation A>T at a site corresponding to position 138 of an amino acid sequence of *Escherichia coli* EPSPS, compared to *Escherichia coli* EPSPS.

Alternatively, it can be understood that when the amino acid sequence of the plant EPSPS mutant is aligned with the amino acid sequence of *Escherichia coli* EPSPS, the amino acid sequence of the plant EPSPS mutant has a mutation from amino acid residue A to T (abbreviated to A138T) at a position corresponding to position 138 of *Escherichia coli* EPSPS.

Further, in some embodiments of the present disclosure, *Escherichia coli* EPSPS has an amino acid sequence as set forth in SEQ ID NO: 1.

In other words, when the amino acid sequence of the plant EPSPS mutant is aligned with the amino acid sequence of *Escherichia coli* EPSPS as set forth in SEQ ID NO: 1, the amino acid sequence of the plant EPSPS mutant has a mutation from amino acid residue A to T at a position corresponding to position 138 of SEQ ID NO: 1.

Further, in some embodiments of the present disclosure, the amino acid sequence of the plant EPSPS mutant further has, corresponding to *Escherichia coli* EPSPS, at least one mutation selected from the group consisting of: K85I, G96A, and P101S.

It can be understood from the mutation K85I that the amino acid sequence of the plant EPSPS mutant has a mutation from amino acid residue K to I at a position corresponding to position 85 of *Escherichia coli* EPSPS, when the amino acid sequence of the plant EPSPS mutant is aligned with the amino acid sequence of *Escherichia coli* EPSPS.

It can be understood from the mutation G96A that the amino acid sequence of the plant EPSPS mutant has a mutation from amino acid residue G to A at a position corresponding to position 96 of *Escherichia coli* EPSPS, when the amino acid sequence of the plant EPSPS mutant is aligned with the amino acid sequence of *Escherichia coli* EPSPS.

It can be understood from the mutation P101S that the amino acid sequence of the plant EPSPS mutant has a mutation from amino acid residue P to S at a position corresponding to position 101 of *Escherichia coli* EPSPS, when the amino acid sequence of the plant EPSPS mutant is aligned with the amino acid sequence of *Escherichia coli* EPSPS.

One or any combination of the mutations K85I, G96A, and P101S combined with the mutation A138T can enhance the glyphosate resistance of the plant EPSPS mutant and maintain the biological enzymatic activity of the plant EPSPS mutant.

Further, in some embodiments of the present disclosure, the plant EPSPS mutant is derived from any one of wheat, rice, barley, oats, corn (or maize), sorghum, millet, buckwheat, *Panicum miliaceum*, mung bean, broad bean, pea, lentil, sweet potato, potato, cotton, soybean, oilseed rape, sesame, peanut, sunflower, radish, carrot, turnip, beet, celery cabbage, mustard, cabbage, broccoli, Chinese kale, cucumber, zucchini, pumpkin, wax gourd, bitter gourd, *Luffa aegyptiaca*, Armenian cucumber, watermelon, melon, tomato, eggplant, chili (or pepper), kidney bean, cowpea, edamame, Chinese leek, green onion, onion, leek, spinach, celery, edible amaranth, lettuce, garland chrysanthemum, daylily, grape, strawberry, beet, sugar cane, tobacco, alfalfa, pasture grass, turf grass, tea, and cassava.

In other words, the plant EPSPS mutant according to the present disclosure is obtained by the above-mentioned mutation of wild-type EPSPS derived from one of wheat, rice, barley, oats, corn, sorghum, millet, buckwheat, *Panicum miliaceum*, mung bean, broad bean, pea, lentil, sweet potato, potato, cotton, soybean, oilseed rape, sesame, peanut, sunflower, radish, carrot, turnip, beet, celery cabbage, mustard, cabbage, broccoli, Chinese kale, cucumber, zucchini, pumpkin, wax gourd, bitter gourd, *Luffa aegyptiaca*, Armenian cucumber, watermelon, melon, tomato, eggplant, chili, kidney bean, cowpea, edamame, Chinese leek, green onion, onion, leek, spinach, celery, edible amaranth, lettuce, garland chrysanthemum, daylily, grape, strawberry, beet, sugar cane, tobacco, alfalfa, pasture grass, turf grass, tea, and cassava, which retains the plant-derived characteristics. An encoding gene encoding the plant EPSPS mutant can be used in breeding crop varieties resistant to glyphosate. For example, the breeding purpose may be achieved by using a transgenic or genetic modification method. Compared with the prior art mode of transformation of a glyphosate-resistant gene from a microorganism, a plant-derived glyphosate-resistant gene is used directly for transformation or used as a template for genome editing, which has more reliable biological safety, contributes to widespread application of new glyphosate-resistant varieties, and improves public acceptance.

Preferably, in some embodiments of the present disclosure, the plant EPSPS mutant is derived from rice (*Oryza sativa*), and the plant EPSPS mutant has an amino acid sequence as set forth in SEQ ID NO: 6. The plant EPSPS mutant set forth in SEQ ID NO: 6 is *Oryza sativa* EPSPS mutant I. The *Oryza sativa* EPSPS mutant I has a mutation A155(138)T relative to an amino acid sequence of wild-type *Oryza sativa* EPSPS set forth in SEQ ID NO: 5.

It can be understood from the A155(138)T mutation that, compared to wild-type *Oryza sativa* EPSPS, the *Oryza sativa* EPSPS mutant has a mutation from amino acid residue A to T at position 155 of SEQ ID NO: 5, which corresponds to position 138 of *Escherichia coli* EPSPS.

Preferably, in some embodiments of the present disclosure, the plant EPSPS mutant is derived from rice, and the amino acid sequence of the plant EPSPS mutant further has the mutation G96A corresponding to *Escherichia coli* EPSPS.

Further preferably, in some embodiments of the present disclosure, the plant EPSPS mutant has an amino acid sequence as set forth in SEQ ID NO: 7.

The plant EPSPS mutant set forth in SEQ ID NO: 7 is *Oryza sativa* EPSPS mutant II. The *Oryza sativa* EPSPS mutant II has two mutations G111(96)A and A155(138)T relative to the amino acid sequence of wild-type *Oryza sativa* EPSPS set forth in SEQ ID NO: 5.

Further preferably, in some embodiments of the present disclosure, the plant EPSPS mutant has an amino acid sequence as set forth in SEQ ID NO: 8.

As the plant EPSPS mutant set forth in SEQ ID NO: 8, the *Oryza sativa* EPSPS mutant has two mutations G111(96)A and P116(101)S relative to the amino acid sequence of wild-type *Oryza sativa* EPSPS set forth in SEQ ID NO: 5.

Further preferably, in some embodiments of the present disclosure, the plant EPSPS mutant has an amino acid sequence as set forth in SEQ ID NO: 9.

As the plant EPSPS mutant set forth in SEQ ID NO: 9, the *Oryza sativa* EPSPS mutant has three mutations G111(96)A, P116(101)S, and A155(138)T relative to the amino acid sequence of wild-type *Oryza sativa* EPSPS set forth in SEQ ID NO: 5.

It can be understood from the G111(96)A mutation that, compared to wild-type *Oryza sativa* EPSPS, the *Oryza sativa* EPSPS mutant II has a mutation from amino acid residue G to A at position 111 of SEQ ID NO: 5, which corresponds to position 96 of *Escherichia coli* EPSPS.

It can be understood from the A155(138)T mutation that, compared to wild-type *Oryza sativa* EPSPS, the *Oryza sativa* EPSPS mutant II has a mutation from amino acid residue A to T at position 155 of SEQ ID NO: 5, which corresponds to position 138 of *Escherichia coli* EPSPS.

Further, in some embodiments of the present disclosure, the plant EPSPS mutant is derived from corn (*Zea mays*), and the plant EPSPS mutant comprises an amino acid sequence having the following mutations corresponding to *Escherichia coli* EPSPS: K85I, G96A, and P101S.

Further, in some embodiments of the present disclosure, the plant EPSPS mutant has an amino acid sequence as set forth in SEQ ID NO: 3.

The plant EPSPS mutant set forth in SEQ ID NO: 3 is a *Zea mays* EPSPS mutant. The *Zea mays* EPSPS mutant has three mutations K94(85)I, G105(96)A, and P110(101)S relative to an amino acid sequence of wild-type *Zea mays* EPSPS set forth in SEQ ID NO: 12.

Further, in some embodiments of the present disclosure, the plant EPSPS mutant has an amino acid sequence as set forth in SEQ ID NO: 13.

The plant EPSPS mutant set forth in SEQ ID NO: 13 is a *Zea mays* EPSPS mutant. The *Zea mays* EPSPS mutant has four mutations K94(85)I, G105(96)A, P110(101)S, and A149(138)T relative to the amino acid sequence of wild-type *Zea mays* EPSPS set forth in SEQ ID NO: 12.

It can be understood from the K94(85)I mutation that, compared to wild-type *Zea mays* EPSPS, the *Zea mays* EPSPS mutant has a mutation from amino acid residue K to I at position 94 of SEQ ID NO: 12, which corresponds to position 85 of *Escherichia coli* EPSPS.

It can be understood from the G105(96)A mutation that, compared to wild-type *Zea mays* EPSPS, the *Zea mays* EPSPS mutant has a mutation from amino acid residue G to A at position 105 of SEQ ID NO: 12, which corresponds to position 96 of *Escherichia coli* EPSPS.

It can be understood from the P110(101)S mutation that, compared to wild-type *Zea mays* EPSPS, the *Zea mays* EPSPS mutant has a mutation from amino acid residue P to S at position 110 of SEQ ID NO: 12, which corresponds to position 101 of *Escherichia coli* EPSPS.

It can be understood from the A149(138)T mutation that, compared to wild-type *Zea mays* EPSPS, the *Zea mays* EPSPS mutant has a mutation from amino acid residue A to T at position 149 of SEQ ID NO: 12, which corresponds to position 138 of *Escherichia coli* EPSPS.

Further, in some embodiments of the present disclosure, the plant EPSPS mutant is derived from wheat (*Triticum aestivum*), and the plant EPSPS mutant comprises an amino acid sequence having the following mutations corresponding to *Escherichia coli* EPSPS: G96A and P101S, having an amino acid sequence as set forth in SEQ ID NO: 4.

Further, in some embodiments of the present disclosure, the plant EPSPS mutant has an amino acid sequence as set forth in SEQ ID NO: 11.

The plant EPSPS mutant set forth in SEQ ID NO: 11 is a *Triticum aestivum* EPSPS mutant. The *Triticum aestivum* EPSPS mutant has three mutations G113(96)A, P118(101)S, and A157(138)T relative to an amino acid sequence of wild-type *Triticum aestivum* EPSPS set forth in SEQ ID NO: 10.

It can be understood from the G113(96)A mutation that, compared to wild-type *Triticum aestivum* EPSPS, the *Triticum aestivum* EPSPS mutant has a mutation from amino acid residue G to A at position 113 of SEQ ID NO: 10, which corresponds to position 96 of *Escherichia coli* EPSPS.

It can be understood from the P118(101)S mutation that, compared to wild-type *Triticum aestivum* EPSPS, the *Triticum aestivum* EPSPS mutant has a mutation from amino acid residue P to S at position 118 of SEQ ID NO: 10, which corresponds to position 101 of *Escherichia coli* EPSPS.

It can be understood from the A157(138)T mutation that, compared to wild-type *Triticum aestivum* EPSPS, the *Triticum aestivum* EPSPS mutant has a mutation from amino acid residue A to T at position 157 of SEQ ID NO: 10, which corresponds to position 138 of *Escherichia coli* EPSPS.

In a further aspect, the present disclosure provides an encoding gene that encodes the plant EPSPS mutant described above.

According to the degeneracy of codons, a nucleotide coding sequence of the EPSPS mutant can be easily obtained on the basis of the amino acid sequence of the plant EPSPS mutant described above. Any encoding gene capable of encoding the plant EPSPS mutant described above will fall within the scope of protection of the present disclosure.

Further, in some embodiments of the present disclosure, the encoding gene described above is set forth in SEQ ID NO: 15, 17, 22, or 25.

The sequence set forth in SEQ ID NO: 17 represents an *Oryza sativa* EPSPS mutant II-encoding gene, encoding the *Oryza sativa* EPSPS mutant set forth in SEQ ID NO: 7.

The sequence set forth in SEQ ID NO: 25 represents a *Zea mays* EPSPS mutant-encoding gene, encoding the *Zea mays* EPSPS mutant set forth in SEQ ID NO: 13.

The sequence set forth in SEQ ID NO: 22 represents a *Triticum aestivum* EPSPS mutant-encoding gene, encoding the *Triticum aestivum* EPSPS mutant set forth in SEQ ID NO: 11.

The sequence set forth in SEQ ID NO: 15 represents an *Oryza sativa* EPSPS mutant I-encoding gene, encoding the *Oryza sativa* EPSPS mutant I set forth in SEQ ID NO: 6.

Substitution of one or more nucleotides can be readily made by those skilled in the art on the basis of the sequence of the above-mentioned encoding gene according to the degeneracy of codons to obtain a corresponding derivative sequence so as to encode the plant EPSPS mutant according to the present disclosure. Therefore, a corresponding derivative sequence encoding the plant EPSPS mutant according to the present disclosure obtained by substitution of one or more nucleotides on the basis of the sequence of the above-mentioned encoding gene will also fall within the scope of protection of the present disclosure.

In a further aspect, the present disclosure provides a vector containing the encoding gene described above.

Further, in some embodiments of the present disclosure, the vector may be a cloning vector or an expression vector. Further, in some embodiments of the present disclosure, the expression vector may be a prokaryotic expression vector such as pADV5 vector, or a eukaryotic expression vector. Further, in some embodiments of the present disclosure, the eukaryotic expression vector is a plant expression vector such as pGVP1 vector.

It will be readily understood that any suitable vector can be selected as required by those skilled in the art as a tool for carrying the above-mentioned encoding gene and will fall within the scope of protection of the present disclosure.

In a further aspect, the present disclosure provides a recombinant bacterium or recombinant cell containing the vector described above.

Further, in some embodiments of the present disclosure, the recombinant bacterium may be a coccus, a bacillus such as *Escherichia coli*, or a spirillum, or may be an autotrophic bacterium or heterotrophic bacterium.

Further, in some embodiments of the present disclosure, the recombinant cell may be a prokaryotic cell or a eukaryotic cell; further, in some embodiments of the present disclosure, the eukaryotic cell may be an animal cell or a plant cell; further, in some embodiments of the present disclosure, the plant cell may be a dicotyledonous plant cell or a monocotyledonous plant cell.

It will be readily understood that any suitable bacterium or cell can be selected as required by those skilled in the art as a host for the above-mentioned encoding gene and will fall within the scope of protection of the present disclosure.

In a further aspect, the present disclosure provides use of the plant EPSPS mutant described above in the breeding a glyphosate-resistant plant.

Further, in some embodiments of the present disclosure, the above-mentioned use comprises: transforming a vector into a target plant, the vector containing an encoding gene encoding the plant EPSPS mutant.

For example, a vector containing an *Oryza sativa* EPSPS-encoding gene set forth in SEQ ID NO: 17 is transformed into, for example, rice callus tissue, which is cultured and differentiated into a complete rice plant, whereby transgenic glyphosate-resistant rice can be cultivated.

Further, in some embodiments of the present disclosure, the above-mentioned use comprises: modifying an endogenous EPSPS gene of a target plant to encode the plant EPSPS mutant.

For example, the *Oryza sativa* EPSPS-encoding gene set forth in SEQ ID NO: 17 is used partially or wholly as a template for modification of an endogenous EPSPS gene of a rice genome, whereby non-transgenic rice can be cultivated.

Further, in some embodiments of the present disclosure, the above-mentioned use includes: mutagenizing plant cells, tissues, individuals, or populations to encode the plant EPSPS mutant.

For example, the *Oryza sativa* EPSPS-encoding gene set forth in SEQ ID NO: 17 is used as a guide for mutagenesis such as chemical or radiation mutagenesis of a rice material, whereby rice with the mutated endogenous EPSPS gene can be cultivated.

Further, in some embodiments of the present disclosure, the target plant is any one of wheat, rice, barley, oats, corn, sorghum, millet, buckwheat, *Panicum miliaceum*, mung bean, broad bean, pea, lentil, sweet potato, potato, cotton, soybean, oilseed rape, sesame, peanut, sunflower, radish, carrot, turnip, beet, celery cabbage, mustard, cabbage, broccoli, Chinese kale, cucumber, zucchini, pumpkin, wax gourd, bitter gourd, *Luffa aegyptiaca*, Armenian cucumber, watermelon, melon, tomato, eggplant, chili, kidney bean, cowpea, edamame, Chinese leek, green onion, onion, leek, spinach, celery, edible amaranth, lettuce, garland chrysanthemum, daylily, grape, strawberry, beet, sugar cane, tobacco, alfalfa, pasture grass, turf grass, tea, and cassava.

It will be readily understood that crop varieties to be cultivated can be selected as required by those skilled in the art, and any crop varieties, in which the plant EPSPS mutants according to the present disclosure and/or genes encoding the same are used, will fall within the scope of protection of the present disclosure.

It should be noted that the alignment means used in the protein sequence alignment involved in the present disclosure is the online alignment tool Clustal, which is available on line. The results obtained by using other sequence alignment tools (such as DNAMAN, wherein the relevant parameter settings are set by default) are substantially consistent with the results obtained by the online alignment tool Clustal.

In summary, the present disclosure provides a plant EPSPS mutant, the plant EPSPS mutant comprising an amino acid sequence having a mutation A>T at a site corresponding to position 138 of an amino acid sequence of *Escherichia coli* EPSPS, compared to *Escherichia coli* EPSPS. This mutation site corresponds to position 155 of wild-type *Oryza sativa* EPSPS, position 149 of wild-type *Zea mays* EPSPS, and position 157 of wild-type *Triticum*

*aestivum* EPSPS. The mutation can significantly increase the glyphosate resistance of different mutants of EPSPS of various plants while improving the biological enzymatic catalytic activity of the mutants. All of plants or recombinant bacteria transformed with the plant EPSPS mutants can grow normally. The plant EPSPS mutants can be used not only for breeding transgenic crops, but also for breeding glyphosate-resistant non-transgenic plants such as rice, tobacco, soybean, corn, wheat, cotton, sorghum, and the like, and thus have wide application prospects.

The features and performance of the present disclosure will be described in further detail below in connection with examples.

Example 1

This example provides a plant EPSPS mutant, which is derived from rice and is named *Oryza sativa* EPSPS mutant I, which is obtained by mutation of wild-type *Oryza sativa* EPSPS (having an amino acid sequence as set forth in SEQ ID NO: 5), and which has an amino acid sequence as set forth in SEQ ID NO: 6.

The *Oryza sativa* EPSPS mutant I has a mutation A155(138)T relative to the amino acid sequence of wild-type *Oryza sativa* EPSPS set forth in SEQ ID NO: 5.

That is to say, compared to wild-type *Oryza sativa* EPSPS, the *Oryza sativa* EPSPS mutant I has a mutation from G to A at amino acid residue 155, which corresponds to position 138 of *Escherichia coli* EPSPS.

This example further provides an *Oryza sativa* EPSPS mutant I-encoding gene encoding the *Oryza sativa* EPSPS mutant I described above, which has a nucleotide sequence as set forth in SEQ ID NO: 15.

Both the *Oryza sativa* EPSPS mutant I-encoding gene and the *Oryza sativa* EPSPS mutant I according to the example of the present disclosure can be obtained by a chemical synthesis method.

Example 2

This example provides a plant EPSPS mutant, which is derived from rice and named an *Oryza sativa* EPSPS mutant II, which is obtained by mutation of wild-type *Oryza sativa* EPSPS (having an amino acid sequence as set forth in SEQ ID NO: 5), and which has an amino acid sequence as set forth in SEQ ID NO: 7.

The *Oryza sativa* EPSPS mutant II has two mutations G111(96)A and A155(138)T relative to the amino acid sequence of wild-type *Oryza sativa* EPSPS set forth in SEQ ID NO: 5.

That is to say, as shown in FIG. 5 (FIG. 5 illustrates a partial result of the alignment of amino acid sequences of *Escherichia coli* EPSPS, *Oryza sativa* EPSPS mutant II, and wild-type *Oryza sativa* EPSPS, wherein Ec-EPSPS WT represents *Escherichia coli* EPSPS; Os-EPSPS M represents *Oryza sativa* EPSPS mutant II; Os-EPSPS WT represents wild-type *Oryza sativa* EPSPS) compared to wild-type *Oryza sativa* EPSPS, the *Oryza sativa* EPSPS mutant II has a mutation from G to A at position 111 (the 111 st amino acid residual), which corresponds to position 96 of *Escherichia coli* EPSPS (SEQ ID NO: 1), and has a mutation from A to T at position 155, which corresponds to position 138 of *Escherichia coli* EPSPS (at sites as indicated by arrows in FIG. 5).

This example further provides an *Oryza sativa* EPSPS mutant II-encoding gene encoding the *Oryza sativa* EPSPS mutant II described above, which has a nucleotide sequence as set forth in SEQ ID NO: 17.

Both the *Oryza sativa* EPSPS mutant II-encoding gene and the *Oryza sativa* EPSPS mutant II according to the example of the present disclosure can be obtained by a chemical synthesis method.

Example 3

This example provides a plant EPSPS mutant, which is derived from corn and is a *Zea mays* EPSPS mutant, which is obtained by mutation of wild-type *Zea mays* EPSPS (having an amino acid sequence as set forth in SEQ ID NO: 12), and which has an amino acid sequence as set forth in SEQ ID NO: 13.

The *Zea mays* EPSPS mutant has four mutations K94(85)I, G105(96)A, P110(101)S, and A149(138)T relative to the amino acid sequence of wild-type *Zea mays* EPSPS set forth in SEQ ID NO: 12.

That is to say, as shown in FIG. 6 (FIG. 6 illustrates a partial result of the alignment of amino acid sequences of *Escherichia coli* EPSPS, the *Zea mays* EPSPS mutant, and wild-type *Zea mays* EPSPS, wherein Ec-EPSPS WT represents *Escherichia coli* EPSPS; Z-EPSPS M represents the *Zea mays* EPSPS mutant; Z-EPSPS WT represents wild-type *Zea mays* EPSPS), compared to wild-type *Zea mays* EPSPS, the *Zea mays* EPSPS mutant has a mutation from K to I at position 94, which corresponds to position 85 of *Escherichia coli* EPSPS, has a mutation from G to A at position 105, which corresponds to position 96 of *Escherichia coli* EPSPS, has a mutation from P to S at position 110, which corresponds to position 101 of *Escherichia coli* EPSPS, and has a mutation from A to T at position 149, which corresponds to position 138 of *Escherichia coli* EPSPS (at sites as indicated by arrows in FIG. 6).

The example of the present disclosure further provides a *Zea mays* EPSPS mutant-encoding gene encoding the *Zea mays* EPSPS mutant described above, which has a nucleotide sequence as set forth in SEQ ID NO: 25.

Both the *Zea mays* EPSPS mutant-encoding gene and the *Zea mays* EPSPS mutant according to the example of the present disclosure can be obtained by a chemical synthesis method.

Example 4

This example provides a plant EPSPS mutant, which is derived from wheat and is a *Triticum aestivum* EPSPS mutant, which is obtained by mutation of wild-type *Triticum aestivum* EPSPS (having an amino acid sequence as set forth in SEQ ID NO: 10), and which has an amino acid sequence as set forth in SEQ ID NO: 11.

The *Triticum aestivum* EPSPS mutant has three mutations G113(96)A, P118(101)S, and A157(138)T relative to the amino acid sequence of wild-type *Triticum aestivum* EPSPS set forth in SEQ ID NO: 10.

That is to say, as shown in FIG. 7 (FIG. 7 illustrates a partial result of the alignment of amino acid sequences of *Escherichia coli* EPSPS, the *Triticum aestivum* EPSPS mutant, and wild-type *Triticum aestivum* EPSPS, wherein Ec-EPSPS WT represents *Escherichia coli* EPSPS; T-EPSPS M represents the *Triticum aestivum* EPSPS mutant; T-EPSPS WT represents wild-type *Triticum aestivum* EPSPS), compared to wild-type *Triticum aestivum* EPSPS, the *Triticum aestivum* EPSPS mutant has a mutation from G to A at position 113, which corresponds to position 96 of *Escherichia coli* EPSPS (SEQ ID NO: 1), has a mutation from P to S at position 118, which corresponds to position 101 of *Escherichia coli* EPSPS, and has a mutation from A to T at position 157, which corresponds to position 138 of *Escherichia coli* EPSPS (at sites as indicated by arrows in FIG. 7).

The example of the present disclosure further provides a *Triticum aestivum* EPSPS mutant-encoding gene encoding the *Triticum aestivum* EPSPS mutant described above, which has a nucleotide sequence as set forth in SEQ ID NO: 22.

Both the *Triticum aestivum* EPSPS mutant-encoding gene and the *Triticum aestivum* EPSPS mutant according to the example of the present disclosure can be obtained by a chemical synthesis method.

Example 5

An *Escherichia coli* strain transformed with the *Oryza sativa* EPSPS mutant I-encoding gene according to Example 1 was used as Experimental Group 1 (having only the A155(138)T mutation).

An *Escherichia coli* strain transformed with a gene encoding an *Oryza sativa* EPSPS mutant not having the A155 (138)T mutation but only having the G111(96)A mutation (having a nucleotide sequence as set forth in SEQ ID NO: 16, where the encoded *Oryza sativa* EPSPS mutant with a single mutation had an amino acid sequence as set forth in SEQ ID NO: 2) was used as Experimental Group 2.

An *Escherichia coli* strain transformed with the *Oryza sativa* EPSPS mutant II-encoding gene according to Example 2 was used as Experimental Group 3 (having the G111(96)A mutation and A155(138)T mutation).

An *Escherichia coli* strain transformed with a wild-type *Oryza sativa* EPSPS-encoding gene (SEQ ID NO: 14, encoding wild-type *Oryza sativa* EPSPS set forth in SEQ ID NO: 5) was used as a control group.

The glyphosate resistance of the *Oryza sativa* EPSPS mutant I-encoding gene and the encoded *Oryza sativa* EPSPS mutant I in *Escherichia coli*, and the glyphosate resistance of the *Oryza sativa* EPSPS mutant II-encoding gene and the encoded *Oryza sativa* EPSPS mutant II in *Escherichia coli* were verified by detecting the growth statuses of the transformed *Escherichia coli* in media containing different concentrations of glyphosate (0 mM, 1 mM, 2 mM, 20 mM) (media obtained by using M9 as a basal medium and then adding certain concentrations of antibiotics Spec (Spectinomycin), Gen (Gentamycin), and Amp (Ampicillin) and different concentrations of glyphosate).

Here, the M9 basal medium may be prepared with reference to the following method:

5×M9 salt solution: which was prepared by weighing 6.78 g of $Na_2HPO_4$, 3.0 g of $KH_2PO_4$, 0.5 g of NaCl, and 1.0 g of $NH_4Cl$ and adding $ddH_2O$ to a volume of 200 ml, and sterilized at high temperature and at high pressure;

20% glucose: which was prepared by weighing 20 g of glucose that was then dissolved in 80 ml of $ddH_2O$ to a constant volume of 100 ml, and filtered and sterilized;

1.0 M $MgSO_4$: which was prepared by weighing 24.6 g of $MgSO_4.7H_2O$ that was then dissolved in 80 ml of $ddH_2O$ to a constant volume of 100 ml, and sterilized;

1.0 M $CaCl_2$: which was prepared by weighing 11.1 g of $CaCl_2$ that was then dissolved in 80 ml of $ddH_2O$ to a constant volume of 100 ml, and sterilized;

1000 ml of M9 basal medium was prepared by using 200 ml of the 5×M9 salt solution, 20 ml of 20% glucose, 2 ml of 1.0 M $MgSO_4$, and 0.1 ml of 1.0 M $CaCl_2$ and making up the volume to 1000 ml with $ddH_2O$.

Here, the *Escherichia coli* strain used was an double-knockout *Escherichia coli* strain (*Escherichia coli* strain DH5a from which an EPSPS gene and a C-P Lyase gene were knocked out, named EDCE, which may be prepared by a method with reference to Chinese Patent Application No. 2016103256926).

The detection was carried out by a method well known in the art, which was briefly described below. Gene encoding *Oryza sativa* EPSPS mutants was synthesized by a chemical synthesis method, wherein enzymatic digestion sites (PacI and SbfI) were introduced at both ends of the gene. The gene were enzymatically cleaved and then ligated in the presence of ligase to an expression vector (e.g., pADV5 vector having a structure as shown in FIG. 4) subjected to the same enzymatic digestion treatment, and then were transformed into the double-knockout *Escherichia coli* strain. After verification, positive clones were picked out and inoculated and grown in media containing glyphosate. The growth statuses were observed.

The results were shown in FIG. 1. Experimental Groups 1-3 and the control group could grow in the medium containing 0 mM glyphosate, but Experimental Groups 1-3 grew faster and better, indicating that the *Oryza sativa* EPSPS mutant had stronger EPSPS enzymatic activity than wild-type *Oryza sativa* EPSPS.

In the medium containing 1 mM glyphosate, the control group could not grow, and Experimental Group 1, Experimental Group 2, and Experimental Group 3 all showed bacterial plaques, indicating that all of the *Oryza sativa* EPSPS mutant I having only the A155(138)T mutation according to Example 1, the *Oryza sativa* EPSPS mutant with a single mutation having an amino acid sequence as set forth in SEQ ID NO: 6, and the *Oryza sativa* EPSPS mutant II having the two mutations G111(96)A and A155(138)T had glyphosate resistance.

In the media containing 2 mM and 20 mM glyphosate, the control group, Experimental Group 1, and Experimental Group 2 could not grow, while Experimental Group 3 could grow normally and showed bacterial plaques. This indicated that the *Oryza sativa* EPSPS mutant II-encoding gene and the *Oryza sativa* EPSPS mutant II according to Example 2 could impart glyphosate resistance to the *Escherichia coli* strain double-deficient in EPSPS and C-P Lyase, so that it was kept in a growing state in the medium containing up to 20 mM glyphosate.

The above results indicated that the single mutation A155(138)T could impart glyphosate resistance to *Oryza sativa* EPSPS mutants, and had enhanced glyphosate resistant characteristics when combined with the G111(96)A mutation.

Example 6

An *Escherichia coli* strain transformed with the *Zea mays* EPSPS mutant-encoding gene according to Example 3 was used as an experimental group.

An *Escherichia coli* strain transformed with a wild-type *Zea mays* EPSPS-encoding gene (SEQ ID NO: 23, encoding wild-type *Zea mays* EPSPS set forth in SEQ ID NO: 12) was used as Control Group 1.

An *Escherichia coli* strain transformed with a gene encoding a *Zea mays* EPSPS mutant with three mutations not having the A149(138)T mutation but only having the three mutations K94(85)I, G105(96)A, and P110(101)S (having a nucleotide sequence as set forth in SEQ ID NO: 24, where the encoded *Zea mays* EPSPS mutant with three mutations had an amino acid sequence as set forth in SEQ ID NO: 3) was used as Control Group 2.

The growth statuses of the transformed *Escherichia coli* strains in media containing different concentrations of glyphosate (0, 1, 20, 50 mM) were detected to verify the glyphosate resistance of the *Zea mays* EPSPS mutant-encoding gene and the encoded *Zea mays* EPSPS mutant in *Escherichia coli*. Here, the *Escherichia coli* strain used was double-knockout *Escherichia coli* (*Escherichia coli* strain DH5a from which an EPSPS gene and a C-P Lyase gene were knocked out, named EDCE, which may be prepared by a method with reference to Chinese Patent Application. 2016103256926).

Figure 2:
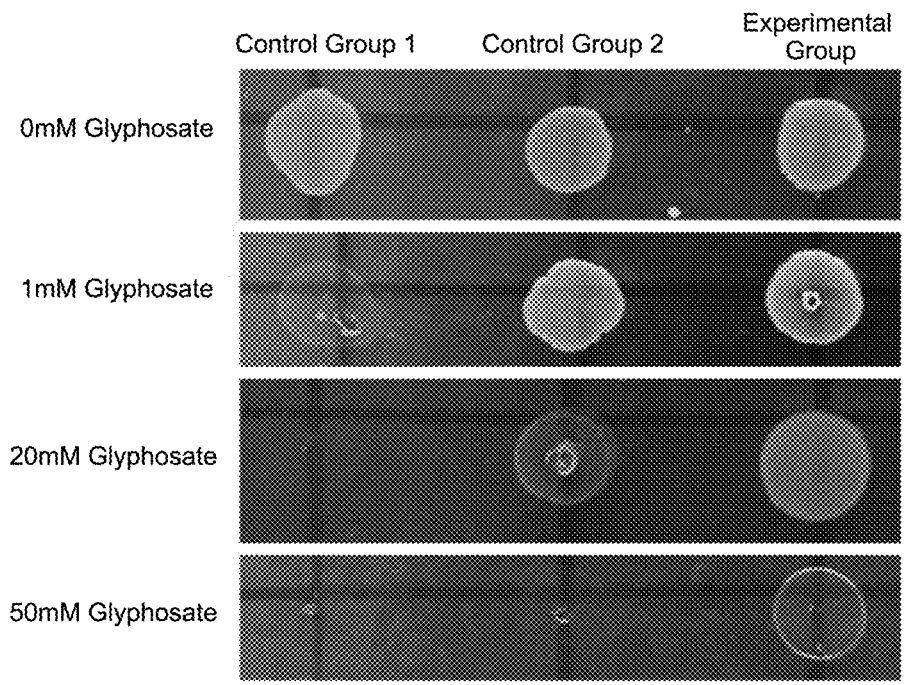
FIG. 2 is a view showing results of growth of an *Escherichia coli* strain transformed with a gene encoding a *Zea mays* EPSPS mutant according to Example 2 in media containing different concentrations of glyphosate in Example 6 of the present disclosure.

The results were shown in FIG. 2. Each of the experimental group and the control groups could grow normally in the media containing 0 mM and 1 mM glyphosate.

In the medium containing 20 mM glyphosate, the experimental group and Control Group 2 could grow normally, but Control Group 2 grew slowly.

In the medium containing 50 mM glyphosate, the experimental group could still grow significantly, while Control Group 2 failed to grow. This indicated that the *Zea mays* EPSPS mutant-encoding gene and the *Zea mays* EPSPS mutant according to Example 3 could impart glyphosate resistance to the *Escherichia coli* strain double-deficient in EPSPS and C-P Lyase, so that it was kept in a growing state in the medium containing up to 50 mM glyphosate.

The above results further showed that the single mutation A149(138)T combined with the K94(85)I, G105(96)A, and P110(101)S mutations had enhanced glyphosate resistant characteristics.

Example 7

An *Escherichia coli* strain transformed with the *Triticum aestivum* EPSPS mutant-encoding gene according to Example 4 was used as an experimental group.

An *Escherichia coli* strain transformed with a wild-type *Triticum aestivum* EPSPS-encoding gene (SEQ ID NO: 20, encoding wild-type *Triticum aestivum* EPSPS set forth in SEQ ID NO: 10 was used as Control Group 1.

An *Escherichia coli* strain transformed with a gene encoding a *Triticum aestivum* EPSPS mutant with double mutations not having the A157(138)T mutation but only having the two mutations G113(96)A and P118(101)S (having a nucleotide sequence as set forth in SEQ ID NO: 21, where the encoded *Triticum aestivum* EPSPS mutant with double mutations had an amino acid sequence as set forth in SEQ ID NO: 4) was used as Control Group 2.

The growth statuses of the transformed *Escherichia coli* strains in media containing different concentrations of glyphosate (0, 1, 20 mM) were detected to verify the glyphosate resistance of the *Triticum aestivum* EPSPS mutant-encoding gene and the encoded *Triticum aestivum* EPSPS mutant in *Escherichia coli*. Here, the *Escherichia coli* strain used was double-knockout *Escherichia coli* (*Escherichia coli* strain DH5a from which an EPSPS gene and a C-P Lyase gene were knocked out, named EDCE, which may be prepared by a method with reference to Chinese Patent Application. 2016103256926).

The results were shown in FIG. 3. Each of the experimental group and the control groups could grow normally in the medium containing 0 mM glyphosate.

In the medium containing 1 mM glyphosate, Control Group 1 failed to grow normally, the experimental group and Control Group 2 could grow normally, but Control Group 2 grew slowly.

In the medium containing 20 mM glyphosate, the experimental group could still grow significantly, while Control Group 2 failed to grow. This indicated that the *Triticum aestivum* EPSPS mutant-encoding gene and the *Triticum aestivum* EPSPS mutant according to Example 4 could impart glyphosate resistance to the *Escherichia coli* strain double-deficient in EPSPS and C-P Lyase, so that it was kept in a growing state in the medium containing up to 20 mM glyphosate.

The above results further showed that the single mutation A157(138)T had enhanced glyphosate resistant characteristics when combined with the G113(96)A and P118(101)S mutations.

Example 8

The glyphosate resistance of the EPSPS mutants of the above examples in transgenic rice was detected by the following method.

Figure 8:
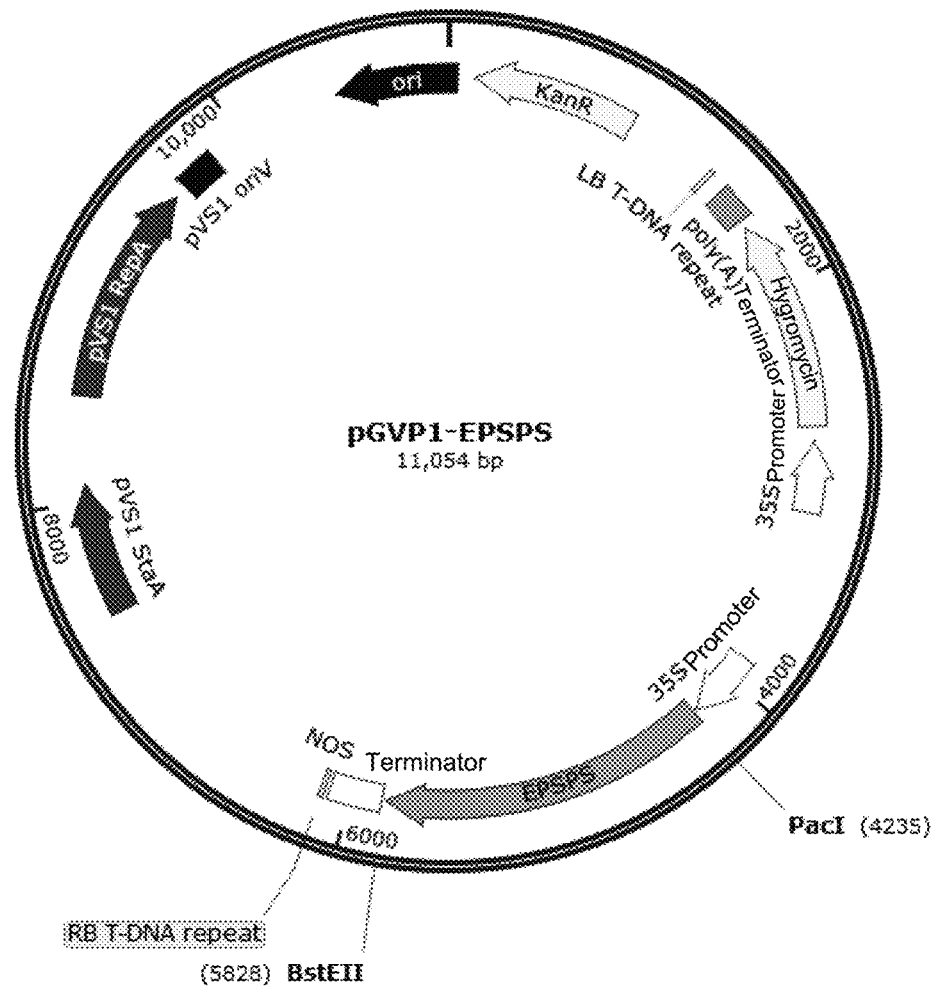
FIG. 8 is a schematic structural view of a pGVP1-EPSPS vector according to Example 8 of the present disclosure.

Plasmids of monoclonal resistant strain comprising pADV5-EPSPS of Examples 1-4 (containing the EPSPS mutant genes) were extracted in accordance with a conventional method. They were subjected to double enzymatic digestion with PacI and BstEII to recover small fragments, and then the small fragments were ligated, using T4 DNA ligase, to a pGVP1 vector subjected to double enzymatic digestion in the same manner, to obtain a pGVP1-EPSPS vector having a structure as shown in FIG. 8.

The pGVP1-EPSPS vector was transformed into EHA105 (*Agrobacterium tumefaciens*) competent cells, and single clones were picked out for colony PCR detection to obtain positive strains. Then, the positive strains were inoculated into and propagated in 1 mL of a YEP medium containing 50 μg·mL$^{-1}$ kanamycin and 50 μg·mL$^{-1}$ rifampicin, and stored at −80° C. or used in subsequent experiments.

Transformation in Rice:

400 ul of a strain containing the target gene vector stored at −80° C. was added to a culture dish with a solid medium containing YEP+50 μg/mL rifampicin+50 μg/mL kanamycin and cultured in the dark at 28° C. for 24 hours, and then the bacterium was added to an infection medium and adjusted to OD=0.2 as an infection solution.

Disinfection and Pre-culture: seeds of mature rice (Nipponbare) were manually dehulled. Full seeds with no bacterial plaques were selected and disinfected in accordance with the following steps: the seeds were placed in a 50 ml sterile centrifuge tube and disinfected with the added 70% ethanol in water for 30 seconds, ethanol solution was poured out, and the seeds were washed once with sterile water; 10 to 20 ml of 2.6% sodium hypochlorite solution was added to soak and disinfect the seeds for 20 minutes. The sodium hypochlorite solution was poured out, and the seeds were soaked and washed with sterile water for 6 or 7 times, for 3 minutes each time.

Induction and Subculture: the seeds were placed on and blotted with sterile filter paper, and the mature embryos were placed in an induction medium, with 12 embryos per dish. After the operation was completed, the culture dishes were sealed with parafilm and underwent culturing in the dark at 30° C. for 21 to 28 days. Callus tissue was transferred to a fresh medium and continued to be cultured for about 7 to 14 days. Spherical callus tissue with a dimension of 1 to 2 mm was taken as an infection receptor.

Infection and Co-Culture:

The callus tissue was placed into a centrifuge tube or culture cup, infected in the prepared *Agrobacterium* suspension added thereto for 10 minutes, and shaken several times during the period; the bacterial solution was poured out, the callus tissue was taken out and placed on sterile filter paper for absorbing the bacterial solution from its surface (for about 30 minutes); the callus tissue was placed on sterile filter paper in culture dishes and cultured in the dark at 25° C. for 2 or 3 days.

Recovery Culture: the co-cultured callus tissue was inoculated on a recovery medium and cultured in the dark at 30° C. for 5 to 7 days.

Primary Screening: the callus was transferred to screening medium 1 (51) and cultured in the dark at 30° C. for 14 days.

Secondary Screening: the callus was then transferred to screening medium 2 (S2) and cultured in the dark at 30° C. for 14 days.

Primary Differentiation: the screened resistant callus tissue was transferred to a differentiation medium and cultured for about 21 days at 30° C. under exposure to light for 19 hours.

Secondary Differentiation: new young shoots were selected and moved to a fresh differentiation medium and continued to be cultured for about 21 days.

When the new seedlings grew to about 2 cm, they were moved to a rooting medium and cultured for 3 to 4 weeks at 30° C. under exposure to light (for 16/8 h). When roots appeared and the seedlings grew to 7 to 10 cm, they were taken out from the medium, washed for removing the medium from the roots, moved to seedling cultivation trays, continued to be cultured for about 10 days, and then moved to a greenhouse or field.

Medium Formulas:

Induction Medium: NB Basal Medium [N6 macronutrients+MS iron salt solution+B5 micronutrients and organic nutrients]+casein hydrolysate 0.3 g/L+L-proline 2.787 g/L+sucrose 30 g/L+2,4-D 4 mg/L+agar 8 g/L, pH 5.8.

Infection Medium: NB Basal Medium [N6 macronutrients+MS iron salt solution+B5 micronutrients and organic nutrients]+L-proline 0.7 g/L+sucrose 68.4 g/L+glucose 36 g/L+2,4-D 2 mg/L, pH 5.2 (in a small autoclave at 115° C.), with AS 20 mg/L added when in use.

Co-culture Medium: NB Basal Medium [N6 macronutrients+MS iron salt solution+B5 micronutrients and organic nutrients]+casein hydrolysate 0.3 g/L+L-proline 2.787 g/L+sucrose 30 g/L+2,4-D 1 mg/L, pH 5.2, with AS 20 mg/L added when in use.

Recovery Medium: NB Basal Medium [N6 macronutrients+MS iron salt solution+B5 micronutrients and organic nutrients]+glutamine 0.2 g/L+L-proline 2.787 g/L+sucrose 30 g/L+2,4-D 4 mg/L+agar 8 g/L, pH 5.8. After sterilization, Cefotaxime (100 mg/L)+Timentin 100 mg/L+Vancomycin 50 mg/L were added.

Screening Medium 1 (51): NB Basal Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH 5.8. After sterilization, Cefotaxime 100 mg/L+Timentin 100 mg/L+Vancomycin 50 mg/L were added. A screening agent (Glyphosate 400 mg/L, or hygromycin 50 mg/L) was added.

Screening Medium 2 (S2): NB Basal Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH 5.8. After sterilization, Cefotaxime 100 mg/L+Timentin 100 mg/L+Vancomycin 50 mg/L were added. A screening agent (Glyphosate 50 to 400 mg/L, or hygromycin 30 mg/L) was added.

Differentiation Medium (F): MS Basal Medium [MS macronutrients+iron salt solution+micronutrients and organic nutrients]+glutamine 0.2 g/L+sucrose 30 g/L+sorbitol 30 g/L+agar 8 g/L, pH 5.8. After sterilization, Cefotaxime 200 mg/L+KT 2 mg/L+NAA 0.02 mg/L+Glyphosate 1 to 5 mg/L were added.

A screening agent (Glyphosate 1 to 5 mg/L, or hygromycin 20 mg/L) was added.

Rooting Medium: 1/2 MS Basal Medium [MS macronutrients, iron salt solution, micronutrients and organic nutrients]+inositol 0.1 g/L+sucrose 30 g/L+agar 8 g/L, pH 5.8. After sterilization, Cefotaxime 100 mg/L and NAA 0.2 mg/L were added.

Detection of Transgenic Plants:

Rice plants transformed with EPSPS mutant genes were detected by a PCR method, for which forward and reverse detection primers were designed according to the sequence of the pGVP1-EPSPS vector and rice internal reference genes. The sequence was as follows:

For a partial sequence of the vector:
CaMV15: 5'-GGTGGCTCCTACAAATGCCATC-3' (SEQ ID NO: 26);
CTS3: 5'-GAGCCAATTAACGTCATCCCAC-3' (SEQ ID NO: 27), with an amplified fragment size of 452 bp.

For rice internal reference gene:
OsF: 5'-GCTTCTGACCAGCCCATTATTCTGC-3' (SEQ ID NO: 28);
OsR: 5'-CCCTCAAGGGTAAGCTCATCTCTCTTC-3' (SEQ ID NO: 29), with an amplified fragment size of 629 bp.

Genomic DNAs of rice plants transformed with pGVP1-EPSPS genes were extracted, respectively, and normalized to 100 ng/μL.

PCR Detection System: 10 μL 2×TsINGKe, 2 μL primer mixture (10 μmol/L of OsF, OsR, CaMV15, and CTS3, each in an amount of 0.5 μL), 1 μL genomic DNA template (100 ng/μL), 7 μL ddH$_2$O.

PCR Detection Procedure: 94° C., 3 min; 94° C., 30 s; 62° C., 30 s; 72° C., 45 s; 30 cycles; 72° C., 10 min; hold at 12° C.

The PCR amplification products were electrophoresed on a 1.5% agarose gel, and those with bands at position 452 bp and at position 629 bp were transgenic positive plants.

In this example, the glyphosate resistance of the EPSPS mutants in rice transgenic plants was verified. The experimental method was carried out as follows:

The transplanted transgenic rice seedlings were evenly arranged in the same experimental area (to avoid overlapping of leaves). Area sizes occupied by the experimental group and the control group were calculated, and glyphosate was sprayed at 1,060 g/ha (0.106 g/m$^2$) as a 1× dose according to the area size. The 2× dose was 2,120 g/ha, the 5× dose was 5,300 g/ha, and the 20× dose was 21,200 g/ha.

Commercially available 41% glyphosate ammonium salt with name Roundup was used. A corresponding volume of glyphosate ammonium salt Roundup was taken according to the above-mentioned spray concentration, then diluted with a 20 times larger volume of water, and thereafter sprayed evenly on the plants of the experimental group and the control group. After the surfaces of the leaves were dried, the plants were moved to a greenhouse or cultivated outside.

The statistics of glyphosate resistance were made based on the following standard: a plant was a highly glyphosate resistant plant indicated with "+++", if the plant did not exhibit any damage caused by glyphosate and grew normally; a plant was a moderately glyphosate resistant plant indicated with "++", if the plant exhibited slightly yellowing leaves and grew a little slow; a plant was a low glyphosate resistant plant indicated with "+", if the plant had some withered leaves and grew very slowly; and a plant was a non-glyphosate resistant plant (without glyphosate resistance) indicated with "−", if the plant was withered or dead (Table 1).

The growth statuses of each group of plants were observed and recorded on day 10 after they were sprayed with 1× glyphosate, and the surviving plants were sprayed with 2× glyphosate. The growth statuses of each group of plants were observed and recorded after another 10 days, and the surviving plants were sprayed with 5× glyphosate. The growth statuses of each group of plants were observed and recorded after additional 10 days, and the surviving plants were sprayed with 20× glyphosate. The growth statuses of each group of plants were observed and recorded after further 10 days. The results were shown in Table 1, where numerical values in rows of −, +, ++, and +++ indicate corresponding plant numbers, and "%++&+++" expressed a percentage of the moderately and highly glyphosate resistant plants in the total number of the plants observed.

TABLE 1

| Glyphosate Dose | Resistance | R0 | R1 | R2 | R3 | R4 | R5 | T1 | T2 |
| --- | --- | --- | --- | --- | --- | --- | --- | --- | --- |
| 1X Dose | + | 1 | 8 | 2 | 1 | 0 | 0 | 1 | 2 |
|  | ++ | 0 | 7 | 1 | 9 | 0 | 0 | 7 | 4 |
|  | +++ | 0 | 11 | 8 | 25 | 23 | 23 | 14 | 20 |
|  | % ++&+++ | 0.0 | 58.1 | 69.2 | 70.8 | 88.5 | 92.0 | 70.0 | 75.0 |
| 2X Dose | − | 31 | 26 | 3 | 16 | 3 | 4 | 15 | 10 |
|  | + | 0 | 5 | 2 | 0 | 2 | 0 | 4 | 3 |
|  | ++ | 0 | 0 | 2 | 4 | 1 | 1 | 1 | 2 |
|  | +++ | 0 | 0 | 6 | 28 | 20 | 20 | 10 | 17 |
|  | % ++&+++ | 0.0 | 0.0 | 61.5 | 66.7 | 80.8 | 84.0 | 36.7 | 59.4 |
| 5X Dose | − | 31 | 30 | 5 | 24 | 5 | 4 | 15 | 11 |
|  | + | 0 | 1 | 2 | 0 | 3 | 2 | 4 | 5 |
|  | ++ | 0 | 0 | 3 | 13 | 1 | 2 | 7 | 14 |
|  | +++ | 0 | 0 | 3 | 11 | 17 | 17 | 4 | 2 |
|  | % ++&+++ | 0.0 | 0.0 | 46.2 | 50.0 | 69.2 | 76.0 | 36.7 | 50.0 |
| 20X Dose | − | 31 | 31 | 7 | 30 | 10 | 5 | 19 | 14 |
|  | + | 0 | 0 | 4 | 7 | 3 | 1 | 7 | 11 |
|  | ++ | 0 | 0 | 1 | 7 | 10 | 6 | 4 | 7 |
|  | +++ | 0 | 0 | 1 | 4 | 3 | 13 | 0 | 0 |
|  | %++&+++ | 0.0 | 0.0 | 15.4 | 22.9 | 50.0 | 76.0 | 13.3 | 21.9 |

As could be seen from the results of Table 1:

After sprayed with 1× glyphosate, rice seedlings transformed with the wild-type *Oryza sativa* EPSPS R0 (SEQ ID NO: 14) all had no resistance, and died except for one severely damaged plant, but rice seedlings transformed with the *Oryza sativa* EPSPS mutant R1 (SEQ ID NO: 15) containing the A155(138)T mutation exhibited significantly better glyphosate resistance than that of R0, 58.1% of them were moderately or highly resistant, and all of them survived at 2× X and 5× glyphosate doses, indicating that the single-mutantion mutant containing A155(138)T exhibited significantly better glyphosate resistance than the wild type.

Rice seedlings transformed with the *Oryza sativa* EPSPS mutant R3 (SEQ ID NO: 17) containing G111(96)A and A155(138)T exhibited similar levels of glyphosate resistance at 1×, 2×, and 5× glyphosate doses compared with rice seedlings transformed with the *Oryza sativa* EPSPS mutant R2 (SEQ ID NO: 16) containing G111(96)A, but at the 20× glyphosate dose, R3 resulted in moderately and highly resistant plants in a proportion of 22.9%, which was significantly higher than 15.4% resulting from R2, indicating that the A155(138)T mutation could further increase the glyphosate resistance provided by the G111(96)A mutation.

Rice seedlings transformed with the *Oryza sativa* EPSPS mutant R5 (SEQ ID NO: 19) containing G111(96)A, P116 (101)S, and A155(138)T exhibited higher levels of glyphosate resistance at each of 1×, 2×, 5×, and 20× glyphosate doses than those of rice seedlings transformed with the *Oryza sativa* EPSPS mutant R4 (SEQ ID NO: 18) containing G111(96)A and P116(101)S, and R5 resulted in moderately and highly resistant plants in a proportion of up to 76% especially at the 20× glyphosate dose, indicating that the A155(138)T mutation could further increase the glyphosate resistance provided by the G111(96)A and P116(101)S mutations.

Rice seedlings transformed with the *Triticum aestivum* EPSPS mutant T2 (SEQ ID NO: 22) containing G113(96)A, P118(101)S, and A157(138)T exhibited higher levels of glyphosate resistance at each of 1×, 2×, 5×, and 20× glyphosate doses than those of rice seedlings transformed with the *Triticum aestivum* EPSPS mutant T1 (SEQ ID NO: 21) containing G113(96)A and P118(101)S, indicating that the A157(138)T mutation could further increase the glyphosate resistance provided by the G113(96)A and P118(101)S mutations.

The above results fully show that an amino acid sequence of a plant EPSPS mutant having a mutation A138T at a site corresponding to position 138 of *Escherichia coli* EPSPS compared to the sequence of *Escherichia coli* EPSPS can impart or increase the glyphosate resistance of the plant EPSPS mutant in a plant.

In summary, the plant EPSPS mutants (SEQ ID NO: 6, 7, 9, 11, and 13) and genes encoding the same (SEQ ID NO: 15, 17, 19, 22, and 25) according to the present disclosure have higher glyphosate resistance and complete biological enzymatic activity compared to the wild-type plant EPSPS and genes encoding the same (SEQ ID NO: 5, 10, and 12). In addition, the plant EPSPS mutants and genes encoding the same according to the present disclosure are derived from rice, corn, and wheat varieties per se, rather than microorganisms, and thus can be suitable for transformation into various plant varieties such as rice, tobacco, soybean, corn, cotton, sorghum, wheat, and other plants and can be used over a wider scope. Moreover, according to the sequences of the genes encoding the plant EPSPS mutants proposed in the present disclosure, the genes can be used in the cultivation of new glyphosate-resistant rice varieties (by a non-transgenic method) to obtain non-transgenic conventional varieties resistant to glyphosate and to improve the public acceptance of new varieties.

The above description is merely illustrative of preferred embodiments of the present disclosure and is not intended to limit the present disclosure. It will be understood by those skilled in the art that various modifications and variations can be made to the present disclosure. Any modifications, equivalent alternatives, improvements and so on made within the spirit and principle of the present disclosure are to be included in the scope of protection of the present disclosure.

What is claimed is:

1. A mutant 5-enolpyruvylshikimate-3-phosphate synthase (EPSPS) protein comprising an alanine to threonine substitution at a position corresponding to position 138 of SEQ ID NO: 1, wherein the mutant EPSPS protein is derived from a plant.

2. The mutant EPSPS protein of claim 1, further comprising at least one substitution selected from the group consisting of a lysine to isoleucine substitution at a position corresponding to position 85 of SEQ ID NO: 1; a glycine to alanine substitution at a position corresponding to position 96 of SEQ ID NO: 1, and a proline to serine substitution at a position corresponding to position 101 of SEQ ID NO: 1.

3. The mutant EPSPS protein of claim 1, wherein the protein is derived from any one of rice, tobacco, soybean, corn, wheat, cotton, or sorghum.

4. The mutant EPSPS protein of claim 1, wherein the protein is derived from rice and further comprises a glycine to alanine substitution at a position corresponding to position 96 of SEQ ID NO: 1.

5. The mutant EPSPS protein of claim 4, wherein the protein comprises the amino acid sequence of SEQ ID NO: 7.

6. The mutant EPSPS protein of claim 1, wherein the protein is derived from corn and further comprises a lysine to isoleucine substitution at a position corresponding to position 85 of SEQ ID NO: 1, a glycine to alanine substitution at a position corresponding to position 96 of SEQ ID NO: 1, and a proline to serine substitution at a position corresponding to position 101 of SEQ ID NO: 1.

7. The mutant EPSPS protein of claim 6, wherein the protein comprises the amino acid sequence of SEQ ID NO: 13.

8. The mutant EPSPS protein of claim 1, wherein the protein is derived from wheat and further comprises a glycine to alanine substitution at a position corresponding to position 96 of SEQ ID NO: 1, and a proline to serine substitution at a position corresponding to position 101 of SEQ ID NO: 1.

9. The mutant EPSPS protein of claim 8, wherein the protein comprises the amino acid sequence of SEQ ID NO: 11.

10. A nucleic acid molecule encoding the mutant EPSPS protein of claim 1.

11. A method for preparing a glyphosate resistant plant, comprising transforming a target plant with the nucleic acid molecule of claim 10 or with a vector containing said molecule to obtain the glyphosate resistant plant.

12. The method of claim 11, wherein the target plant is selected from the group consisting of wheat, rice, barley, oats, corn, sorghum, millet, buckwheat, mung bean, broad bean, pea, lentil, sweet potato, potato, cotton, soybean, oilseed rape, sesame, peanut, sunflower, radish, carrot, turnip, beet, celery cabbage, mustard, cabbage, broccoli, Chinese kale, cucumber, zucchini, pumpkin, wax gourd, bitter gourd, loofah, Armenian cucumber, watermelon, melon, tomato, eggplant, chili, kidney bean, cowpea, edamame, Chinese leek, green onion, onion, leek, spinach, celery, edible amaranth, lettuce, garland chrysanthemum, daylily, grape, strawberry, beet, sugar cane, tobacco, alfalfa, pasture grass, turf grass, tea, and cassava.

* * * * *

```
                              SEQUENCE LISTING

<160> NUMBER OF SEQ ID NOS: 29

<210> SEQ ID NO 1
<211> LENGTH: 427
<212> TYPE: PRT
<213> ORGANISM: Escherichia coli

<400> SEQUENCE: 1

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350
```

```
Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
                420                 425

<210> SEQ ID NO 2
<211> LENGTH: 454
<212> TYPE: PRT
<213> ORGANISM: Artificial Sequence
<220> FEATURE:
<223> OTHER INFORMATION: Oryza sativa EPSPS mutant with only G111(96)A
      mutation

<400> SEQUENCE: 2

Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
                20                  25                  30

Lys Ser Leu Ser Asn Arg Ile Leu Leu Ser Ala Leu Ser Glu Gly
            35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Ala Thr
            100                 105                 110

Ala Met Arg Pro Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
            195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270
```

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
            290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
                340                 345                 350

Ala Asp Gly Pro Thr Ala Ile Arg Asp Val Ala Ser Trp Arg Val Lys
                355                 360                 365

Glu Thr Glu Arg Met Val Ala Ile Arg Thr Glu Leu Thr Lys Leu Gly
            370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
                420                 425                 430

Asp Pro Gly Cys Thr Arg Lys Thr Phe Pro Asn Tyr Phe Asp Val Leu
                435                 440                 445

Ser Thr Phe Val Arg Asn
            450

<210> SEQ ID NO 3
<211> LENGTH: 448
<212> TYPE: PRT
<213> ORGANISM: Artificial Sequence
<220> FEATURE:
<223> OTHER INFORMATION: Zea mays EPSPS mutant with mutations K94(85)I,
      G105(96)A, and P110(101)S

<400> SEQUENCE: 3

Met Ala Val Gln Ala Gly Ala Glu Glu Ile Val Leu Gln Pro Ile Lys
1               5                   10                  15

Glu Ile Ser Gly Thr Val Lys Leu Pro Gly Ser Lys Ser Leu Ser Asn
            20                  25                  30

Arg Ile Leu Leu Leu Ala Ala Leu Ser Glu Gly Thr Thr Val Val Asp
        35                  40                  45

Asn Leu Leu Asn Ser Glu Asp Val His Tyr Met Leu Gly Ala Leu Arg
    50                  55                  60

Thr Leu Gly Leu Ser Val Glu Ala Asp Lys Ala Ala Lys Arg Ala Val
65                  70                  75                  80

Val Val Gly Cys Gly Gly Lys Phe Pro Val Glu Asp Ser Ile Glu Glu
                85                  90                  95

Val Gln Leu Phe Leu Gly Asn Ala Ala Thr Ala Met Arg Ser Leu Thr
            100                 105                 110

Ala Ala Val Thr Ala Ala Gly Gly Asn Ala Thr Tyr Val Leu Asp Gly
        115                 120                 125

Val Pro Arg Met Arg Glu Arg Pro Ile Gly Asp Leu Val Val Gly Leu
    130                 135                 140

Lys Gln Leu Gly Ala Asp Val Asp Cys Phe Leu Gly Thr Asp Cys Pro
145                 150                 155                 160

```
Pro Val Arg Val Asn Gly Ile Gly Gly Leu Pro Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Asp Lys Leu
        195                 200                 205

Ile Ser Ile Pro Tyr Val Glu Met Thr Leu Arg Leu Met Glu Arg Phe
210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
        435                 440                 445

<210> SEQ ID NO 4
<211> LENGTH: 456
<212> TYPE: PRT
<213> ORGANISM: Artificial Sequence
<220> FEATURE:
<223> OTHER INFORMATION: Triticum aestivum EPSPS mutant with mutations
      G113(96)A and P118(101)S

<400> SEQUENCE: 4

Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
50                  55                  60
```

```
Tyr Met Leu Glu Ala Leu Glu Ala Leu Gly Leu Ser Val Glu Ala Asp
 65                  70                  75                  80

Lys Val Ala Lys Arg Ala Val Val Gly Cys Gly Gly Arg Phe Pro
                 85                  90                  95

Val Glu Lys Asp Ala Lys Glu Val Lys Leu Phe Leu Gly Asn Ala
             100                 105                 110

Ala Thr Ala Met Arg Ser Leu Thr Ala Val Val Ala Ala Gly Gly
         115                 120                 125

Asn Ala Thr Tyr Val Leu Asp Gly Val Pro Arg Met Arg Glu Arg Pro
130                 135                 140

Ile Gly Asp Leu Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                 165                 170                 175

Gly Leu Pro Gly Gly Lys Val Lys Leu Ser Gly Ser Ile Ser Ser Gln
             180                 185                 190

Tyr Leu Ser Ser Leu Leu Met Ala Ala Pro Leu Ala Leu Glu Asp Val
         195                 200                 205

Glu Ile Glu Ile Asp Lys Leu Ile Ser Val Pro Tyr Val Glu Met
210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gln Lys Tyr Lys Ser Pro
                 245                 250                 255

Gly Asn Ala Tyr Val Glu Gly Asp Ala Ser Ser Ala Ser Tyr Phe Leu
             260                 265                 270

Ala Gly Ala Ala Ile Thr Gly Gly Thr Val Thr Val Glu Gly Cys Gly
         275                 280                 285

Thr Thr Ser Leu Gln Gly Asp Val Lys Phe Ala Glu Val Leu Glu Met
290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                 325                 330                 335

Asn Met Asn Lys Met Pro Asp Val Ala Met Thr Leu Ala Val Val Ala
             340                 345                 350

Leu Phe Ala Asp Gly Pro Thr Ala Ile Arg Asp Val Ala Ser Trp Arg
         355                 360                 365

Val Lys Glu Thr Glu Arg Met Val Ala Ile Arg Thr Glu Leu Thr Lys
370                 375                 380

Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                 405                 410                 415

Met Ala Met Ala Phe Ser Leu Ala Ala Cys Ala Glu Val Pro Val Thr
             420                 425                 430

Ile Arg Asp Pro Gly Cys Thr Arg Lys Thr Phe Pro Asn Tyr Phe Asp
         435                 440                 445

Val Leu Ser Thr Phe Val Lys Asn
450                 455

<210> SEQ ID NO 5
<211> LENGTH: 454
```

<212> TYPE: PRT
<213> ORGANISM: Oryza sativa

<400> SEQUENCE: 5

```
Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
                20                  25                  30

Lys Ser Leu Ser Asn Arg Ile Leu Leu Leu Ser Ala Leu Ser Glu Gly
            35                  40                  45

Thr Thr Val Val Asp Asn Leu Leu Asn Ser Glu Asp Val His Tyr Met
        50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Gly Thr
                100                 105                 110

Ala Met Arg Pro Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
        130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
                180                 185                 190

Ser Ala Leu Leu Met Ala Ala Pro Leu Ala Leu Gly Asp Val Glu Ile
            195                 200                 205

Glu Ile Ile Asp Lys Leu Ile Ser Ile Pro Tyr Val Glu Met Thr Leu
        210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
                260                 265                 270

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
        290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
                340                 345                 350

Ala Asp Gly Pro Thr Ala Ile Arg Asp Val Ala Ser Trp Arg Val Lys
            355                 360                 365

Glu Thr Glu Arg Met Val Ala Ile Arg Thr Glu Leu Thr Lys Leu Gly
        370                 375                 380

Ala Ser Val Glu Glu Gly Pro Asp Tyr Cys Ile Ile Thr Pro Pro Glu
385                 390                 395                 400
```

```
Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450

<210> SEQ ID NO 6
<211> LENGTH: 454
<212> TYPE: PRT
<213> ORGANISM: Artificial Sequence
<220> FEATURE:
<223> OTHER INFORMATION: Oryza sativa EPSPS mutant with mutation
      A155(138)T

<400> SEQUENCE: 6

Met Ala Ser Asn Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Pro Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Thr Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285
```

```
Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450

<210> SEQ ID NO 7
<211> LENGTH: 454
<212> TYPE: PRT
<213> ORGANISM: Artificial Sequence
<220> FEATURE:
<223> OTHER INFORMATION: Oryza sativa EPSPS mutant with mutations
      G111(96)A and A155(138)T

<400> SEQUENCE: 7

Met Ala Ser Asn Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
            85                  90                  95

Lys Asp Ala Lys Glu Glu Val Gln Leu Phe Leu Gly Asn Ala Ala Thr
            100                 105                 110

Ala Met Arg Pro Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
        130                 135                 140

Asp Leu Val Val Gly Leu Lys Gln Leu Gly Thr Asp Val Asp Cys Phe
145                 150                 155                 160

Leu Gly Thr Glu Cys Pro Pro Val Arg Val Lys Gly Ile Gly Gly Leu
                165                 170                 175
```

```
Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450

<210> SEQ ID NO 8
<211> LENGTH: 454
<212> TYPE: PRT
<213> ORGANISM: Artificial Sequence
<220> FEATURE:
<223> OTHER INFORMATION: Oryza sativa EPSPS mutant with mutations
      G111(96)A and P116(101)S

<400> SEQUENCE: 8

Met Ala Ser Asn Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60
```

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Ala Thr
            100                 105                 110

Ala Met Arg Ser Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
            130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
            195                 200                 205

Glu Ile Ile Asp Lys Leu Ile Ser Ile Pro Tyr Val Glu Met Thr Leu
210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ala Ser Tyr Phe Leu Ala Gly
            260                 265                 270

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
            355                 360                 365

Glu Thr Glu Arg Met Val Ala Ile Arg Thr Glu Leu Thr Lys Leu Gly
            370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
            435                 440                 445

Ser Thr Phe Val Arg Asn
        450

<210> SEQ ID NO 9
<211> LENGTH: 454

<212> TYPE: PRT
<213> ORGANISM: Artificial Sequence
<220> FEATURE:
<223> OTHER INFORMATION: Oryza sativa EPSPS mutant with mutations
      G111(96)A, P116(101)S, and A155(138)T

<400> SEQUENCE: 9

```
Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Ala Thr
                100                 105                 110

Ala Met Arg Ser Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
        130                 135                 140

Asp Leu Val Val Gly Leu Lys Gln Leu Gly Thr Asp Val Asp Cys Phe
145                 150                 155                 160

Leu Gly Thr Glu Cys Pro Pro Val Arg Val Lys Gly Ile Gly Leu
                165                 170                 175

Pro Gly Gly Lys Val Lys Leu Ser Gly Ser Ile Ser Ser Gln Tyr Leu
                180                 185                 190

Ser Ala Leu Leu Met Ala Ala Pro Leu Ala Leu Gly Asp Val Glu Ile
            195                 200                 205

Glu Ile Ile Asp Lys Leu Ile Ser Ile Pro Tyr Val Glu Met Thr Leu
        210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
                420                 425                 430

Asp Pro Gly Cys Thr Arg Lys Thr Phe Pro Asn Tyr Phe Asp Val Leu
            435                 440                 445

Ser Thr Phe Val Arg Asn
        450

<210> SEQ ID NO 10
<211> LENGTH: 456
<212> TYPE: PRT
<213> ORGANISM: Triticum aestivum

<400> SEQUENCE: 10

Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
                20                  25                  30

Gly Ser Lys Ser Leu Ser Asn Arg Ile Leu Leu Leu Ser Ala Leu Ser
            35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
                100                 105                 110

Gly Thr Ala Met Arg Pro Leu Thr Ala Ala Val Val Ala Ala Gly Gly
            115                 120                 125

Asn Ala Thr Tyr Val Leu Asp Gly Val Pro Arg Met Arg Glu Arg Pro
130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
    195                 200                 205

Glu Ile Glu Ile Ile Asp Lys Leu Ile Ser Val Pro Tyr Val Glu Met
210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
            260                 265                 270

Ala Gly Ala Ala Ile Thr Gly Gly Thr Val Thr Val Glu Gly Cys Gly
        275                 280                 285
```

```
Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380

Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455

<210> SEQ ID NO 11
<211> LENGTH: 456
<212> TYPE: PRT
<213> ORGANISM: Artificial Sequence
<220> FEATURE:
<223> OTHER INFORMATION: Triticum aestivum EPSPS mutant with mutations
      G113(96)A, P118(101)S, and A157(138)T

<400> SEQUENCE: 11

Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Gly Cys Gly Gly Arg Phe Pro
                85                  90                  95

Val Glu Lys Asp Ala Lys Glu Glu Val Lys Leu Phe Leu Gly Asn Ala
                100                 105                 110

Ala Thr Ala Met Arg Ser Leu Thr Ala Ala Val Val Ala Ala Gly Gly
            115                 120                 125

Asn Ala Thr Tyr Val Leu Asp Gly Val Pro Arg Met Arg Glu Arg Pro
        130                 135                 140

Ile Gly Asp Leu Val Val Gly Leu Gln Gln Leu Gly Thr Asp Val Asp
145                 150                 155                 160

Cys Phe Leu Gly Thr Asn Cys Pro Pro Val Arg Ile Asn Gly Lys Gly
                165                 170                 175
```

```
Gly Leu Pro Gly Gly Lys Val Lys Leu Ser Gly Ser Ile Ser Ser Gln
                180                 185                 190

Tyr Leu Ser Ser Leu Leu Met Ala Ala Pro Leu Ala Leu Glu Asp Val
            195                 200                 205

Glu Ile Glu Ile Ile Asp Lys Leu Ile Ser Val Pro Tyr Val Glu Met
210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gln Lys Tyr Lys Ser Pro
                245                 250                 255

Gly Asn Ala Tyr Val Glu Gly Asp Ala Ser Ser Ala Ser Tyr Phe Leu
                260                 265                 270

Ala Gly Ala Ala Ile Thr Gly Gly Thr Val Thr Val Glu Gly Cys Gly
                275                 280                 285

Thr Thr Ser Leu Gln Gly Asp Val Lys Phe Ala Glu Val Leu Glu Met
            290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
                340                 345                 350

Leu Phe Ala Asp Gly Pro Thr Ala Ile Arg Asp Val Ala Ser Trp Arg
                355                 360                 365

Val Lys Glu Thr Glu Arg Met Val Ala Ile Arg Thr Glu Leu Thr Lys
370                 375                 380

Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
                420                 425                 430

Ile Arg Asp Pro Gly Cys Thr Arg Lys Thr Phe Pro Asn Tyr Phe Asp
                435                 440                 445

Val Leu Ser Thr Phe Val Lys Asn
    450                 455

<210> SEQ ID NO 12
<211> LENGTH: 448
<212> TYPE: PRT
<213> ORGANISM: Zea mays

<400> SEQUENCE: 12

Met Ala Val Gln Ala Gly Ala Glu Glu Ile Val Leu Gln Pro Ile Lys
1               5                   10                  15

Glu Ile Ser Gly Thr Val Lys Leu Pro Gly Ser Lys Ser Leu Ser Asn
                20                  25                  30

Arg Ile Leu Leu Leu Ala Ala Leu Ser Glu Gly Thr Thr Val Val Asp
            35                  40                  45

Asn Leu Leu Asn Ser Glu Asp Val His Tyr Met Leu Gly Ala Leu Arg
        50                  55                  60

Thr Leu Gly Leu Ser Val Glu Ala Asp Lys Ala Ala Lys Arg Ala Val
65                  70                  75                  80
```

```
Val Val Gly Cys Gly Gly Lys Phe Pro Val Glu Asp Ser Lys Glu Glu
             85                  90                  95

Val Gln Leu Phe Leu Gly Asn Ala Gly Thr Ala Met Arg Pro Leu Thr
            100                 105                 110

Ala Ala Val Thr Ala Ala Gly Gly Asn Ala Thr Tyr Val Leu Asp Gly
            115                 120                 125

Val Pro Arg Met Arg Glu Arg Pro Ile Gly Asp Leu Val Val Gly Leu
130                 135                 140

Lys Gln Leu Gly Ala Asp Val Asp Cys Phe Leu Gly Thr Asp Cys Pro
145                 150                 155                 160

Pro Val Arg Val Asn Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Asp Lys Leu
            195                 200                 205

Ile Ser Ile Pro Tyr Val Glu Met Thr Leu Arg Leu Met Glu Arg Phe
210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
            275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
            355                 360                 365

Ala Ile Arg Thr Glu Leu Thr Lys Leu Gly Ala Ser Val Glu Glu Gly
370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
            435                 440                 445
```

<210> SEQ ID NO 13
<211> LENGTH: 448
<212> TYPE: PRT
<213> ORGANISM: Artificial Sequence
<220> FEATURE:
<223> OTHER INFORMATION: Zea mays EPSPS mutant with mutations K94(85)I,
      G105(96)A, P110(101)S, and A149(138)T

```
<400> SEQUENCE: 13

Met Ala Val Gln Ala Gly Ala Glu Glu Ile Val Leu Gln Pro Ile Lys
1               5                   10                  15

Glu Ile Ser Gly Thr Val Lys Leu Pro Gly Ser Lys Ser Leu Ser Asn
            20                  25                  30

Arg Ile Leu Leu Leu Ala Ala Leu Ser Glu Gly Thr Thr Val Val Asp
        35                  40                  45

Asn Leu Leu Asn Ser Glu Asp Val His Tyr Met Leu Gly Ala Leu Arg
    50                  55                  60

Thr Leu Gly Leu Ser Val Glu Ala Asp Lys Ala Ala Lys Arg Ala Val
65                  70                  75                  80

Val Val Gly Cys Gly Gly Lys Phe Pro Val Glu Asp Ser Ile Glu Glu
                85                  90                  95

Val Gln Leu Phe Leu Gly Asn Ala Ala Thr Ala Met Arg Ser Leu Thr
            100                 105                 110

Ala Ala Val Thr Ala Ala Gly Gly Asn Ala Thr Tyr Val Leu Asp Gly
        115                 120                 125

Val Pro Arg Met Arg Glu Arg Pro Ile Gly Asp Leu Val Val Gly Leu
130                 135                 140

Lys Gln Leu Gly Thr Asp Val Asp Cys Phe Leu Gly Thr Asp Cys Pro
145                 150                 155                 160

Pro Val Arg Val Asn Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Ile Asp Lys Leu
        195                 200                 205

Ile Ser Ile Pro Tyr Val Glu Met Thr Leu Arg Leu Met Glu Arg Phe
    210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415
```

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
        435                 440                 445

<210> SEQ ID NO 14
<211> LENGTH: 1365
<212> TYPE: DNA
<213> ORGANISM: Oryza sativa

<400> SEQUENCE: 14
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga gggcacaaca gtggtggaca acttgctgaa cagtgaggat     180
gttcactaca tgcttgaggc cctgaaagcc ctcgggctct ctgtggaagc agataaagtt     240
gcaaaaagag ctgtagtcgt tggctgtggt ggcaagtttc tgttgagaa ggatgcgaaa      300 gaggaagtgc aactcttctt ggggaacgct ggaactgcaa tgcgaccatt gacagcagcc     360
gtgactgctg ctggtggaaa tgcaacttat gtgcttgatg gagtgccacg aatgagggag     420
agaccgattg gtgacttggt tgtcgggttg aaacaacttg gtgcggatgt cgactgtttc     480
cttggcacta atgcccacc tgttcgtgtc aagggaattg gaggacttcc tggtggcaag     540
gttaagctct ctggttccat cagcagtcag tacttgagtg ccttgctgat ggctgctcct     600
ttggcccttg gggatgtgga gatcgaaatc attgacaaac taatctccat tccttacgtt     660
gaaatgacat tgagattgat ggagcgtttt ggtgtgaagg cagagcattc tgatagttgg     720
gacagattct atattaaggg agggcagaag tacaaatctc ctggaaatgc ctatgttgaa     780
ggtgatgcct caagcgcgag ctatttcttg gctggtgctg caatcactgg aggcactgtg     840
acagttcaag ttgtggtac gaccagtttg cagggtgatg tcaaatttgc tgaggtactt     900
gagatgatgg agcaaaggt tacatggact gacaccagtg taaccgtaac tggtccacca     960
cgtgagcctt atgggaagaa acacctgaaa gctgttgatg tcaacatgaa caaaatgcct     1020
gatgttgcca tgacccttgc cgttgttgca ctcttcgctg atggtccaac tgctatcaga     1080
gatgtggctt cctggagagt aaaggaaacc gaaaggatgg ttgcaattcg gaccgagcta     1140
acaaagctgg gagcatcggt tgaagaaggt cctgactact gcatcatcac cccaccggag     1200
aagctgaaca tcacggcaat cgacacctac gatgatcaca ggatggccat ggccttctcc     1260
ctcgctgcct gcgccgacgt gcccgtgacg atcagggacc tggttgcac ccgcaagacc      1320 ttccccaact acttcgacgt tctaagcact ttcgtcagga actga                    1365

<210> SEQ ID NO 15
<211> LENGTH: 1365
<212> TYPE: DNA
<213> ORGANISM: Artificial Sequence
<220> FEATURE:
<223> OTHER INFORMATION: Coding Oryza sativa EPSPS mutant with mutation
      A155(138)T

<400> SEQUENCE: 15
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga gggcacaaca gtggtggaca acttgctgaa cagtgaggat     180
gttcactaca tgcttgaggc cctgaaagcc ctcgggctct ctgtggaagc agataaagtt     240

```
gcaaaaagag ctgtagtcgt tggctgtggt ggcaagtttc ctgttgagaa ggatgcgaaa         300
gaggaagtgc aactcttctt ggggaacgct gggactgcaa tgcgaccatt gacagcagcc         360
gtgactgctg ctggtggaaa tgcaacttat gtgcttgatg gagtgccacg aatgagggag         420
agaccgattg tgacttggt tgtcgggttg aaacaacttg gtacggatgt cgactgtttc          480
cttggcactg aatgcccacc tgttcgtgtc aagggaattg gaggacttcc tggtggcaag         540
gttaagctct ctggttccat cagcagtcag tacttgagtg ccttgctgat ggctgctcct         600
ttggcccttg gggatgtgga gatcgaaatc attgacaaac taatctccat tccttacgtt         660
gaaatgacat tgagattgat ggagcgtttt ggtgtgaagg cagagcattc tgatagttgg         720
gacagattct atattaaggg agggcagaag tacaaatctc ctggaaatgc ctatgttgaa         780
ggtgatgcct caagcgcgag ctatttcttg gctggtgctg caatcactgg aggcactgtg         840
acagttcaag gttgtggtac gaccagtttg cagggtgatg tcaaatttgc tgaggtactt         900
gagatgatgg gagcaaaggt tacatggact gacaccagtg taaccgtaac tggtccacca         960
cgtgagcctt atgggaagaa acacctgaaa gctgttgatg tcaacatgaa caaaatgcct        1020
gatgttgcca tgaccccttgc cgttgttgca ctcttcgctg atggtccaac tgctatcaga        1080
gatgtggctt cctggagagt aaaggaaacc gaaaggatgg ttgcaattcg gaccgagcta        1140
acaaagctgg gagcatcggt tgaagaaggt cctgactact gcatcatcac cccaccggag        1200
aagctgaaca tcacggcaat cgacacctac gatgatcaca ggatggccat ggccttctcc        1260
ctcgctgcct cgccgacgt gcccgtgacg atcagggacc ctggttgcac ccgcaagacc         1320
ttccccaact acttcgacgt tctaagcact ttcgtcagga actga                        1365
```

<210> SEQ ID NO 16
<211> LENGTH: 1365
<212> TYPE: DNA
<213> ORGANISM: Artificial Sequence
<220> FEATURE:
<223> OTHER INFORMATION: Coding Oryza sativa EPSPS mutant with only G111(96)A mutation

<400> SEQUENCE: 16

```
atggcgtcca acgccgcggc tgcggcggcg aaggcggagg agatcgtgct ccagcccatc          60
agggagatct ccggggcggt tcagctgcca gggtccaagt cgctctccaa caggatcctc         120
ctcctctccg ccctctccga gggcacaaca gtggtggaca acttgctgaa cagtgaggat         180
gttcactaca tgcttgaggc cctgaaagcc ctcgggctct ctgtggaagc agataaagtt         240
gcaaaaagag ctgtagtcgt tggctgtggt ggcaagtttc ctgttgagaa ggatgcgaaa         300
gaggaagtgc aactcttctt ggggaacgct gcgactgcaa tgcgaccatt gacagcagcc         360
gtgactgctg ctggtggaaa tgcaacttat gtgcttgatg gagtgccacg aatgagggag         420
agaccgattg tgacttggt tgtcgggttg aaacaacttg gtacggatgt cgactgtttc          480
cttggcactg aatgcccacc tgttcgtgtc aagggaattg gaggacttcc tggtggcaag         540
gttaagctct ctggttccat cagcagtcag tacttgagtg ccttgctgat ggctgctcct         600
ttggcccttg gggatgtgga gatcgaaatc attgacaaac taatctccat tccttacgtt         660
gaaatgacat tgagattgat ggagcgtttt ggtgtgaagg cagagcattc tgatagttgg         720
gacagattct atattaaggg agggcagaag tacaaatctc ctggaaatgc ctatgttgaa         780
ggtgatgcct caagcgcgag ctatttcttg gctggtgctg caatcactgg aggcactgtg         840
acagttcaag gttgtggtac gaccagtttg cagggtgatg tcaaatttgc tgaggtactt         900
```

```
gagatgatgg gagcaaaggt tacatggact gacaccagtg taaccgtaac tggtccacca    960
cgtgagcctt atgggaagaa acacctgaaa gctgttgatg tcaacatgaa caaaatgcct   1020
gatgttgcca tgaccctttgc cgttgttgca ctcttcgctg atggtccaac tgctatcaga  1080
gatgtggctt cctggagagt aaaggaaacc gaaaggatgg ttgcaattcg gaccgagcta   1140
acaaagctgg gagcatcggt tgaagaaggt cctgactact gcatcatcac cccaccggag   1200
aagctgaaca tcacggcaat cgacacctac gatgatcaca ggatggccat ggccttctcc   1260
ctcgctgcct gcgccgacgt gcccgtgacg atcagggacc ctggttgcac ccgcaagacc   1320
ttccccaact acttcgacgt tctaagcact ttcgtcagga actga                   1365
```

<210> SEQ ID NO 17
<211> LENGTH: 1365
<212> TYPE: DNA
<213> ORGANISM: Artificial Sequence
<220> FEATURE:
<223> OTHER INFORMATION: Coding Oryza sativa EPSPS mutant with mutations G111(96)A and A155(138)T

<400> SEQUENCE: 17

```
atggcgtcca acgccgcggc tgcggcggcg aaggcggagg agatcgtgct ccagcccatc     60
agggagatct ccggggcggt tcagctgcca gggtccaagt cgctctccaa caggatcctc    120
ctcctctccg ccctctccga gggcacaaca gtggtggaca cttgctgaa cagtgaggat    180 gttcactaca tgcttgaggc cctgaaagcc ctcgggctct ctgtggaagc agataaagtt    240
gcaaaaagag ctgtagtcgt tggctgtggt ggcaagtttc ctgttgagaa ggatgcgaaa    300
gaggaagtgc aactcttctt ggggaacgct gcgactgcaa tgcgaccatt gacagcagcc    360
gtgactgctg ctggtggaaa tgcaacttat gtgcttgatg gagtgccacg aatgagggag    420
agaccgattg gtgacttggt tgtcgggttg aaacaacttg gtacggatgt cgactgtttc    480
cttggcactg aatgcccacc tgttcgtgtc aaggaattg aggacttcc tggtggcaag    540 gttaagctct ctggttccat cagcagtcag tacttgagtg ccttgctgat ggctgctcct    600
ttggcccttg gggatgtgga gatcgaaatc attgacaaac taatctccat tccttacgtt    660
gaaatgacat tgagattgat ggagcgtttt ggtgtgaagg cagagcattc tgatagttgg    720
gacagattct atattaaggg agggcagaag tacaaatctc ctggaaatgc ctatgttgaa    780
ggtgatgcct caagcgcgag ctatttcttg gctggtgctg caatcactgg aggcactgtg    840
acagttcaag ttgtggtac gaccagtttg cagggtgatg tcaaatttgc tgaggtactt    900
gagatgatgg gagcaaaggt tacatggact gacaccagtg taaccgtaac tggtccacca    960
cgtgagcctt atgggaagaa acacctgaaa gctgttgatg tcaacatgaa caaaatgcct   1020
gatgttgcca tgaccctttgc cgttgttgca ctcttcgctg atggtccaac tgctatcaga  1080
gatgtggctt cctggagagt aaaggaaacc gaaaggatgg ttgcaattcg gaccgagcta   1140
acaaagctgg gagcatcggt tgaagaaggt cctgactact gcatcatcac cccaccggag   1200
aagctgaaca tcacggcaat cgacacctac gatgatcaca ggatggccat ggccttctcc   1260
ctcgctgcct gcgccgacgt gcccgtgacg atcagggacc ctggttgcac ccgcaagacc   1320
ttccccaact acttcgacgt tctaagcact ttcgtcagga actga                   1365
```

<210> SEQ ID NO 18
<211> LENGTH: 1365
<212> TYPE: DNA
<213> ORGANISM: Artificial Sequence
<220> FEATURE:
<223> OTHER INFORMATION: Coding Oryza sativa EPSPS mutant with mutations
      G111(96)A and P116(101)S

<400> SEQUENCE: 18

| | | | | | |
|---|---|---|---|---|---|
| atggcgtcca | acgccgcggc | tgcggcggcg | aaggcggagg | agatcgtgct | ccagcccatc | 60 |
| agggagatct | ccggggcggt | tcagctgcca | gggtccaagt | cgctctccaa | caggatcctc | 120 |
| ctcctctccg | ccctctccga | gggcacaaca | gtggtggaca | acttgctgaa | cagtgaggat | 180 |
| gttcactaca | tgcttgaggc | cctgaaagcc | ctcgggctct | ctgtggaagc | agataaagtt | 240 |
| gcaaaaagag | ctgtagtcgt | tggctgtggt | ggcaagtttc | ctgttgagaa | ggatgcgaaa | 300 |
| gaggaagtgc | aactcttctt | ggggaacgct | gcgactgcaa | tgcgatcctt | gacagcagcc | 360 |
| gtgactgctg | ctggtggaaa | tgcaacttat | gtgcttgatg | gagtgccacg | aatgagggag | 420 |
| agaccgattg | gtgacttggt | tgtcgggttg | aaacaacttg | gtgcggatgt | cgactgtttc | 480 |
| cttggcactg | aatgcccacc | tgttcgtgtc | aagggaattg | aggacttcc | tggtggcaag | 540 |
| gttaagctct | ctggttccat | cagcagtcag | tacttgagtg | ccttgctgat | ggctgctcct | 600 |
| ttggcccttg | gggatgtgga | gatcgaaatc | attgacaaac | taatctccat | tccttacgtt | 660 |
| gaaatgacat | tgagattgat | ggagcgtttt | ggtgtgaagg | cagagcattc | tgatagttgg | 720 |
| gacagattct | atattaaggg | agggcagaag | tacaaatctc | ctggaaatgc | ctatgttgaa | 780 |
| ggtgatgcct | caagcgcgag | ctatttcttg | gctggtgctg | caatcactgg | aggcactgtg | 840 |
| acagttcaag | gttgtggtac | gaccagtttg | cagggtgatg | tcaaatttgc | tgaggtactt | 900 |
| gagatgatgg | gagcaaaggt | tacatggact | gacaccagtg | taaccgtaac | tggtccacca | 960 |
| cgtgagcctt | atgggaagaa | acacctgaaa | gctgttgatg | tcaacatgaa | caaaatgcct | 1020 |
| gatgttgcca | tgaccccttg | cgttgttgca | ctcttcgctg | atggtccaac | tgctatcaga | 1080 |
| gatgtggctt | cctggagagt | aaaggaaacc | gaaaggatgg | ttgcaattcg | gaccgagcta | 1140 |
| acaaagctgg | gagcatcggt | tgaagaaggt | cctgactact | gcatcatcac | cccaccggag | 1200 |
| aagctgaaca | tcacggcaat | cgacacctac | gatgatcaca | ggatggccat | ggccttctcc | 1260 |
| ctcgctgcct | gcgccgacgt | gcccgtgacg | atcagggacc | ctggttgcac | ccgcaagacc | 1320 |
| ttccccaact | acttcgacgt | tctaagcact | ttcgtcagga | actga | | 1365 |

<210> SEQ ID NO 19
<211> LENGTH: 1365
<212> TYPE: DNA
<213> ORGANISM: Artificial Sequence
<220> FEATURE:
<223> OTHER INFORMATION: Coding Oryza sativa EPSPS mutant with mutations
      G111(96)A, P116(101)S, and A155(138)T

<400> SEQUENCE: 19

| | | | | | |
|---|---|---|---|---|---|
| atggcgtcca | acgccgcggc | tgcggcggcg | aaggcggagg | agatcgtgct | ccagcccatc | 60 |
| agggagatct | ccggggcggt | tcagctgcca | gggtccaagt | cgctctccaa | caggatcctc | 120 |
| ctcctctccg | ccctctccga | gggcacaaca | gtggtggaca | acttgctgaa | cagtgaggat | 180 |
| gttcactaca | tgcttgaggc | cctgaaagcc | ctcgggctct | ctgtggaagc | agataaagtt | 240 |
| gcaaaaagag | ctgtagtcgt | tggctgtggt | ggcaagtttc | ctgttgagaa | ggatgcgaaa | 300 |
| gaggaagtgc | aactcttctt | ggggaacgct | gcgactgcaa | tgcgatcctt | gacagcagcc | 360 |
| gtgactgctg | ctggtggaaa | tgcaacttat | gtgcttgatg | gagtgccacg | aatgagggag | 420 |
| agaccgattg | gtgacttggt | tgtcgggttg | aaacaacttg | gtacggatgt | cgactgtttc | 480 |

-continued

| | |
|---|---|
| cttggcactg aatgcccacc tgttcgtgtc aagggaattg gaggacttcc tggtggcaag | 540 |
| gttaagctct ctggttccat cagcagtcag tacttgagtg ccttgctgat ggctgctcct | 600 |
| ttggcccttg gggatgtgga gatcgaaatc attgacaaac taatctccat tccttacgtt | 660 |
| gaaatgacat tgagattgat ggagcgtttt ggtgtgaagg cagagcattc tgatagttgg | 720 |
| gacagattct atattaaggg agggcagaag tacaaatctc tggaaatgc ctatgttgaa | 780 |
| ggtgatgcct caagcgcgag ctatttcttg gctggtgctg caatcactgg aggcactgtg | 840 |
| acagttcaag gttgtggtac gaccagtttg cagggtgatg tcaaatttgc tgaggtactt | 900 |
| gagatgatgg gagcaaaggt tacatggact gacaccagtg taaccgtaac tggtccacca | 960 |
| cgtgagcctt atgggaagaa cacctgaaa gctgttgatg tcaacatgaa caaaatgcct | 1020 |
| gatgttgcca tgaccttgc cgttgttgca ctcttcgctg atggtccaac tgctatcaga | 1080 |
| gatgtggctt cctggagagt aaaggaaacc gaaaggatgg ttgcaattcg gaccgagcta | 1140 |
| acaaagctgg gagcatcggt tgaagaaggt cctgactact gcatcatcac cccaccggag | 1200 |
| aagctgaaca tcacggcaat cgacacctac gatgatcaca ggatggccat ggccttctcc | 1260 |
| ctcgctgcct gcgccgacgt gcccgtgacg atcagggacc ctggttgcac ccgcaagacc | 1320 |
| ttccccaact acttcgacgt tctaagcact ttcgtcagga actga | 1365 |

<210> SEQ ID NO 20
<211> LENGTH: 1371
<212> TYPE: DNA
<213> ORGANISM: Triticum aestivum

<400> SEQUENCE: 20

| | |
|---|---|
| atggcgacgt ccgtggcggc ccccgcggcg cccgcgggcg ccgaggaggt cgtgctgcag | 60 |
| cccatccgcg agatctccgg cgccgtgcag ctgcccggct ccaagtcgct ctccaaccgg | 120 |
| atcctcctcc tctccgccct ctccgaggga caacggtgg tggataacct gttgaacagt | 180 |
| gaggatgtcc actacatgct tgaggccctg aagcccttg gactctccgt ggaagcagat | 240 |
| aaagttgcaa aaagagctgt ggttgttggc tgtggcggca ggttcccagt cgaaaaggac | 300 |
| gccaaagagg aagtaaagct cttcttgggt aatgctggaa ctgcaatgcg gccactgacg | 360 |
| gcagctgtag tagctgctgg tggaaatgca acttatgtgc ttgatggcgt accaagaatg | 420 |
| agggagcgac ctattggtga cttagttgta ggtttgcaac aactcggcgc agatgtcgat | 480 |
| tgtttccttg gcacaaactg cccacctgtc cgtatcaacg gcaaaggagg tctacctggt | 540 |
| ggcaaggtta agctctctgg ttccattagc agtcaatacc tgagttcctt gctgatggct | 600 |
| gctccttttgg ctcttgagga tgtcgagatt gaaatcattg ataaactgat ctccgttcct | 660 |
| tatgttgaaa tgacattgaa attgatggag catttttggtg tgactgcgga gcattctgat | 720 |
| agttgggaca gattctacat taagggagga caaaaataca gtcccctgg aaatgcctat | 780 |
| gtcgaaggtg atgcctcaag tgcgagctat ttcttggctg gtgctgccat caccggaggg | 840 |
| actgtgactg tcgaaggttg cggcaccact agtttgcagg gtgatgtgaa atttgctgag | 900 |
| gtacttgaaa tgatgggagc aaaggtcaca tggactgaca ctagtgtaac tgttactggc | 960 |
| ccaccgcgtc agcccatttgg aaggaaacac ctaaaagctg ttgatgtcaa catgaacaaa | 1020 |
| atgccagatg tcgcgatgac tctagccgtt gttgccctgt ttgccgatgg tccaaccgct | 1080 |
| atcagagatg ttgcctcctg gagagtgaag gaaactgaaa gaatggtcgc gatccggacc | 1140 |
| gagctgacga agctgggagc aacggtggag gaaggcccgg actactgcat catcacgccg | 1200 |
| ccggagaagc tgaacatcac ggcgatcgac acctacgatg accaccggat ggcgatggcc | 1260 | ttctccctgg cggcctgtgc tgaggtgcca gtcaccatca gggaccctgg atgcacccga     1320 aagaccttcc ccaactactt cgacgtgcta agcaccttcg tcaagaacta g              1371

<210> SEQ ID NO 21
<211> LENGTH: 1371
<212> TYPE: DNA
<213> ORGANISM: Artificial Sequence
<220> FEATURE:
<223> OTHER INFORMATION: Coding Triticum aestivum EPSPS mutant with
      mutations G113(96)A and P118(101)S

<400> SEQUENCE: 21
atggcgacgt ccgtggcggc ccccgcggcg cccgcgggcg ccgaggaggt cgtgctgcag      60
cccatccgcg agatctccgg cgccgtgcag ctgcccggct ccaagtcgct ctccaaccgg     120
atcctcctcc tctccgccct ctccgaggga acaacggtgg tggataacct gttgaacagt     180
gaggatgtcc actacatgct tgaggccctg aagcccttg actctccgt ggaagcagat      240 aaagttgcaa aagagctgt ggttgttggc tgtggcggca ggttcccagt cgaaaaggac      300
gccaaagagg aagtaaagct cttcttgggt aatgctgcga ctgcaatgcg gagcctgacg     360
gcagctgtag tagctgctgg tggaaatgca acttatgtgc ttgatggcgt accaagaatg     420
agggagcgac ctattggtga cttagttgta ggtttgcaac aactcggcgc agatgtcgat     480
tgtttccttg gcacaaactg cccacctgtc cgtatcaacg gcaaggagg tctacctggt      540 ggcaaggtta agctctctgg ttccattagc agtcaatacc tgagttcctt gctgatggct     600
gctcctttgg ctcttgagga tgtcgagatt gaaatcattg ataaactgat ctccgttcct     660
tatgttgaaa tgacattgaa attgatggag cattttggtg tgactgcgga gcattctgat    720
agttgggaca gattctacat taagggagga caaaaataca gtcccctgg aaatgcctat     780 gtcgaaggtg atgcctcaag tgcgagctat tcttggctg tgctgccat caccggaggg      840 actgtgactg tcgaaggttg cggcaccact agtttgcagg tgatgtgaa atttgctgag     900 gtacttgaaa tgatgggagc aaaggtcaca tggactgaca ctagtgtaac tgttactggc     960
ccaccgcgtc agccatttgg aaggaaacac ctaaaagctg ttgatgtcaa catgaacaaa    1020
atgccagatg tcgcgatgac tctagccgtt gttgccctgt ttgccgatgg tccaaccgct    1080
atcagagatg ttgcctcctg gagagtgaag gaaactgaaa gaatggtcgc gatccggacc    1140
gagctgacga agctgggagc aacggtggag gaaggcccgg actactgcat catcacgccg    1200
ccggagaagc tgaacatcac ggcgatcgac acctacgatg accaccggat ggcgatggcc    1260
ttctccctgg cggcctgtgc tgaggtgcca gtcaccatca gggaccctgg atgcacccga    1320
aagaccttcc ccaactactt cgacgtgcta agcaccttcg tcaagaacta g             1371

<210> SEQ ID NO 22
<211> LENGTH: 1371
<212> TYPE: DNA
<213> ORGANISM: Artificial Sequence
<220> FEATURE:
<223> OTHER INFORMATION: Coding Triticum aestivum EPSPS mutant with
      mutations G113(96)A, P118(101)S, and A157(138)T

<400> SEQUENCE: 22
atggcgacgt ccgtggcggc ccccgcggcg cccgcgggcg ccgaggaggt cgtgctgcag      60
cccatccgcg agatctccgg cgccgtgcag ctgcccggct ccaagtcgct ctccaaccgg     120
atcctcctcc tctccgccct ctccgaggga acaacggtgg tggataacct gttgaacagt     180

```
gaggatgtcc actacatgct tgaggccctg gaagcccttg gactctccgt ggaagcagat      240
aaagttgcaa aaagagctgt ggttgttggc tgtggcggca ggttcccagt cgaaaaggac      300
gccaaagagg aagtaaagct cttcttgggt aatgctgcga ctgcaatgcg gagcctgacg      360
gcagctgtag tagctgctgg tggaaatgca acttatgtgc ttgatggcgt accaagaatg      420
agggagcgac ctattggtga cttagttgta ggtttgcaac aactcggcac ggatgtcgat      480
tgtttccttg gcacaaactg cccacctgtc cgtatcaacg gcaaaggagg tctacctggt      540
ggcaaggtta agctctctgg ttccattagc agtcaatacc tgagttcctt gctgatggct      600
gctcctttgg ctcttgagga tgtcgagatt gaaatcattg ataaactgat ctccgttcct      660
tatgttgaaa tgacattgaa attgatggag cattttggtg tgactgcgga gcattctgat      720
agttgggaca gattctacat taagggagga caaaaataca gtcccctgg  aaatgcctat      780 gtcgaaggtg atgcctcaag tgcgagctat ttcttggctg gtgctgccat caccggaggg      840
actgtgactg tcgaaggttg cggcaccact agtttgcagg gtgatgtgaa atttgctgag      900
gtacttgaaa tgatgggagc aaaggtcaca tggactgaca ctagtgtaac tgttactggc      960
ccaccgcgtc agccatttgg aaggaaacac ctaaaagctg ttgatgtcaa catgaacaaa     1020
atgccagatg tcgcgatgac tctagccgtt gttgccctgt tgccgatgg  tccaaccgct     1080 atcagagatg ttgcctcctg gagagtgaag gaaactgaaa gaatggtcgc gatccggacc     1140
gagctgacga agctgggagc aacggtggag gaaggcccgg actactgcat catcacgccg     1200
ccggagaagc tgaacatcac ggcgatcgac acctacgatg accaccggat ggcgatggcc     1260 ttctcccctgg cggcctgtgc tgaggtgcca gtcaccatca gggaccctgg atgcacccga     1320
aagaccttcc ccaactactt cgacgtgcta agcaccttcg tcaagaacta g              1371

<210> SEQ ID NO 23
<211> LENGTH: 1347
<212> TYPE: DNA
<213> ORGANISM: Zea mays

<400> SEQUENCE: 23
atggcggtgc aggcgggtgc cgaggagatc gtgctgcagc ccatcaagga gatctccggc       60
accgtcaagc tgccggggtc caagtcgctt ccaaccggga tcctcctgct cgccgccctg      120
tccgagggga caacagtggt tgataacctg ttgaacagtg aggatgtcca ctacatgctc      180
ggggccttga ggactcttgg tctctctgtc gaagcggaca agctgccaa  aagagctgta      240 gttgttggct gtggtggaaa gttcccagtt gaggattcta agaggaagt  gcagctcttc      300 ttggggaatg ctggaactgc aatgcggcca ttgacagcag ctgttactgc tgctggtgga      360
aatgcaactt acgtgcttga tggagtacca agaatgaggg agagacccat tggcgacttg      420
gttgtcggat tgaagcagct tggtgcagat gttgattgtt tccttggcac tgactgccca      480
cctgttcgtg tcaatggaat cggagggcta cctggtggca aggtcaagct gtctggctcc      540
atcagcagtc agtacttgag tgccttgctg atggctgctc ctttggctct tggggatgtg      600
gagattgaaa tcattgataa attaatctcc attccctacg tcgaaatgac attgagattg      660
atggagcgtt ttggtgtgaa agcagagcat tctgatagct gggacagatt ctacattaag      720
ggaggtcaaa aatacaagtc ccctaaaaat gcctatgttg aaggtgatgc ctcaagcgca      780
agctatttct tggctggtgc tgcaattact ggagggactg tgactgtgga aggttgtggc      840
accaccagtt tgcagggtga tgtgaagttt gctgaggtac tggagatgat gggagcgaag      900
gttacatgga ccgagactag cgtaactgtt actggcccac cgcgggagcc atttgggagg      960
```

```
aaacacctca aggcgattga tgtcaacatg aacaagatgc ctgatgtcgc catgactctt    1020
gctgtggttg ccctctttgc cgatggcccg acagccatca gagacgtggc ttcctggaga    1080
gtaaaggaga ccgagaggat ggttgcgatc cggacggagc taaccaagct gggagcatct    1140
gttgaggaag ggccggacta ctgcatcatc acgccgccgg agaagctgaa cgtgacggcg    1200
atcgacacgt acgacgacca caggatggcc atggccttct cccttgccgc ctgtgccgag    1260
gtccccgtga ccatccggga ccctgggtgc acccggaaga ccttccccga ctacttcgat    1320
gtgctgagca ctttcgtcaa gaattaa                                        1347

<210> SEQ ID NO 24
<211> LENGTH: 1347
<212> TYPE: DNA
<213> ORGANISM: Artificial Sequence
<220> FEATURE:
<223> OTHER INFORMATION: Coding Zea mays EPSPS mutant with mutations
      K94(85)I, G105(96)A, and P110(101)S

<400> SEQUENCE: 24
atggcggtgc aggcgggtgc cgaggagatc gtgctgcagc ccatcaagga gatctccggc     60
accgtcaagc tgccggggtc caagtcgctt tccaaccgga tcctcctgct cgccgccctg    120
tccgagggga caacagtggt tgataacctg ttgaacagtg aggatgtcca ctacatgctc    180
ggggccttga ggactcttgg tctctctgtc gaagcggaca agctgccaa agagctgta     240 gttgttggct gtggtggaaa gttcccagtt gaggattcta tagaggaagt gcagctcttc    300
ttggggaatg ctgcgactgc aatgcggtcc ttgacagcag ctgttactgc tgctggtgga    360
aatgcaactt acgtgcttga tggagtacca agaatgaggg agagacccat ggcgacttg    420 gttgtcggat tgaagcagct tggtgcagat gttgattgtt ccttggcac tgactgccca     480 cctgttcgtg tcaatggaat cggagggcta cctggtggca aggtcaagct gtctggctcc    540
atcagcagtc agtacttgag tgccttgctg atggctgctc ctttggctct tggggatgtg    600
gagattgaaa tcattgataa attaatctcc attccctacg tcgaaatgac attgagattg    660
atggagcgtt ttggtgtgaa agcagagcat tctgatagct gggacagatt ctacattaag    720
ggaggtcaaa aatacaagtc cctaaaaat gcctatgttg aaggtgatgc ctcaagcgca    780
agctatttct tggctggtgc tgcaattact ggagggactg tgactgtgga aggttgtggc    840
accaccagtt tgcagggtga tgtgaagttt gctgaggtac tggagatgat gggagcgaag    900
gttacatgga ccgagactag cgtaactgtt actggcccac cgcgggagcc atttgggagg    960
aaacacctca aggcgattga tgtcaacatg aacaagatgc ctgatgtcgc catgactctt    1020
gctgtggttg ccctctttgc cgatggcccg acagccatca gagacgtggc ttcctggaga    1080
gtaaaggaga ccgagaggat ggttgcgatc cggacggagc taaccaagct gggagcatct    1140
gttgaggaag ggccggacta ctgcatcatc acgccgccgg agaagctgaa cgtgacggcg    1200
atcgacacgt acgacgacca caggatggcc atggccttct cccttgccgc ctgtgccgag    1260
gtccccgtga ccatccggga ccctgggtgc acccggaaga ccttccccga ctacttcgat    1320
gtgctgagca ctttcgtcaa gaattaa                                        1347

<210> SEQ ID NO 25
<211> LENGTH: 1347
<212> TYPE: DNA
<213> ORGANISM: Artificial Sequence
```

<220> FEATURE:
<223> OTHER INFORMATION: Coding Zea mays EPSPS mutant with mutations
K94(85)I, G105(96)A, P110(101)S, and A149(138)T

<400> SEQUENCE: 25

| | |
|---|---|
| atggcggtgc aggcgggtgc cgaggagatc gtgctgcagc ccatcaagga gatctccggc | 60 |
| accgtcaagc tgccggggtc caagtcgctt tccaaccgga tcctcctgct cgccgccctg | 120 |
| tccgagggga caacagtggt tgataacctg ttgaacagtg aggatgtcca ctacatgctc | 180 |
| ggggccttga ggactcttgg tctctctgtc gaagcggaca agctgccaa aagagctgta | 240 |
| gttgttggct gtggtggaaa gttcccagtt gaggattcta tagaggaagt gcagctcttc | 300 |
| ttggggaatg ctgcgactgc aatgcggtcc ttgacagcag ctgttactgc tgctggtgga | 360 |
| aatgcaactt acgtgcttga tggagtacca agaatgaggg agagacccat ggcgacttg | 420 |
| gttgtcggat tgaagcagct tggtacggat gttgattgtt ccttggcac tgactgccca | 480 |
| cctgttcgtg tcaatggaat cggagggcta cctggtggca aggtcaagct gtctggctcc | 540 |
| atcagcagtc agtacttgag tgccttgctg atggctgctc ctttggctct tggggatgtg | 600 |
| gagattgaaa tcattgataa attaatctcc attccctacg tcgaaatgac attgagattg | 660 |
| atggagcgtt ttggtgtgaa agcagagcat tctgatagct gggacagatt ctacattaag | 720 |
| ggaggtcaaa aatacaagtc ccctaaaaat gcctatgttg aaggtgatgc ctcaagcgca | 780 |
| agctatttct tggctggtgc tgcaattact ggagggactg tgactgtgga aggttgtggc | 840 |
| accaccagtt tgcagggtga tgtgaagttt gctgaggtac tggagatgat gggagcgaag | 900 |
| gttacatgga ccgagactag cgtaactgtt actggcccac cgcggagcc atttggagg | 960 |
| aaacacctca aggcgattga tgtcaacatg aacaagatgc tgatgtcgc catgactctt | 1020 |
| gctgtggttg ccctctttgc cgatggcccg acagccatca gagacgtggc ttcctggaga | 1080 |
| gtaaaggaga ccgagaggat ggttgcgatc cggacggagc taaccaagct gggagcatct | 1140 |
| gttgaggaag gccggactac ctgcatcatc acgccgccgg agaagctgaa cgtgacggcg | 1200 |
| atcgacacgt acgacgacca caggatggcc atggccttct cccttgccgc ctgtgccgag | 1260 |
| gtccccgtga ccatccggga ccctgggtgc acccggaaga ccttccccga ctacttcgat | 1320 |
| gtgctgagca ctttcgtcaa gaattaa | 1347 |

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ggtggctcct acaaatgcca tc                                              22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
gagccaatta acgtcatccc ac                                              22

<210> SEQ ID NO 28
<211> LENGTH: 25

```
<212> TYPE: DNA
<213> ORGANISM: Artificial Sequence
<220> FEATURE:
<223> OTHER INFORMATION: Primer

<400> SEQUENCE: 28
gcttctgacc agcccattat tctgc                                    25

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
ccctcaaggg taagctcatc tctcttc                                  27
```